(12) United States Patent
Otsuka et al.

(10) Patent No.: US 11,534,088 B2
(45) Date of Patent: Dec. 27, 2022

(54) OPTICAL MEASURING APPARATUS AND NON-TRANSITORY COMPUTER READABLE MEDIUM

(71) Applicant: FUJIFILM BUSINESS INNOVATION CORP., Tokyo (JP)

(72) Inventors: Tsutomu Otsuka, Kanagawa (JP); Manabu Akamatsu, Kanagawa (JP); Kazuhiro Sakai, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 256 days.

(21) Appl. No.: 16/003,554

(22) Filed: Jun. 8, 2018

(65) Prior Publication Data

US 2019/0059797 A1 Feb. 28, 2019

(30) Foreign Application Priority Data

Aug. 31, 2017 (JP) .............................. JP2017-167269

(51) Int. Cl.
| | | |
|---|---|---|
| *A61B 5/1455* | (2006.01) | |
| *A61B 5/026* | (2006.01) | |
| *A61B 5/145* | (2006.01) | |
| *A61B 5/00* | (2006.01) | |
| *A61B 5/024* | (2006.01) | |
| *A61B 5/0205* | (2006.01) | |

(52) U.S. Cl.
CPC ........ *A61B 5/14552* (2013.01); *A61B 5/0205* (2013.01); *A61B 5/0261* (2013.01); *A61B 5/14542* (2013.01); *A61B 5/681* (2013.01); *A61B 5/6843* (2013.01); *A61B 5/7285* (2013.01); *A61B 5/02433* (2013.01); *A61B 2562/0238* (2013.01)

(58) Field of Classification Search
CPC . A61B 5/14552; A61B 5/14542; A61B 5/681; A61B 5/7285; A61B 5/6843; A61B 5/0205; A61B 5/0261; A61B 5/02433; A61B 2562/0238
See application file for complete search history.

(56) References Cited

U.S. PATENT DOCUMENTS

| | | | |
|---|---|---|---|
| 6,754,515 B1* | 6/2004 | Pologe ............... | A61B 5/14552 600/336 |
| 9,681,830 B2* | 6/2017 | Couronne .......... | A61B 5/14551 |
| 2010/0130842 A1* | 5/2010 | Hayoz .................. | A61B 5/026 600/326 |

(Continued)

FOREIGN PATENT DOCUMENTS

| | | |
|---|---|---|
| JP | 2013-000540 A | 1/2013 |
| WO | 2014/045346 A1 | 3/2014 |
| WO | 2016/087609 A1 | 6/2016 |

OTHER PUBLICATIONS

Jun. 15, 2021 Office Action issued in Japanese Patent Application No. 2017-167269.

*Primary Examiner* — Devin B Henson
*Assistant Examiner* — Justin Xu
(74) *Attorney, Agent, or Firm* — Oliff PLC

(57) ABSTRACT

An optical measuring apparatus includes first and second light-emitting elements that emit light and a controller. Upon detection of the presence of a body by light emitted from the first light-emitting element, the controller performs control so that the second light-emitting element will emit light with an amount for measuring the body.

20 Claims, 14 Drawing Sheets

(56) References Cited

U.S. PATENT DOCUMENTS

| | | | |
|---|---|---|---|
| 2011/0237912 A1 | 9/2011 | Couronne et al. | |
| 2014/0073486 A1* | 3/2014 | Ahmed | A61B 5/02427 |
| | | | 482/9 |
| 2014/0323828 A1* | 10/2014 | Ahmed | A61B 5/681 |
| | | | 600/301 |
| 2015/0046095 A1* | 2/2015 | Takahashi | A61B 5/7257 |
| | | | 702/19 |
| 2015/0335252 A1* | 11/2015 | Hirota | A61B 5/7246 |
| | | | 600/407 |
| 2016/0106325 A1* | 4/2016 | Kang | A61B 5/6802 |
| | | | 600/479 |
| 2017/0000350 A1* | 1/2017 | Kwon | A61B 5/0261 |
| 2017/0017858 A1* | 1/2017 | Roh | G02B 27/48 |
| 2017/0086692 A1* | 3/2017 | Freschl | A61B 5/02438 |
| 2017/0209055 A1* | 7/2017 | Pantelopoulos | A61B 5/7203 |
| 2017/0251936 A1* | 9/2017 | Sawado | A61B 5/02125 |
| 2017/0325729 A1* | 11/2017 | Halbritter | A61B 5/7214 |
| 2020/0100684 A1* | 4/2020 | Lamego | A61B 5/7203 |

* cited by examiner

OPTICAL MEASURING APPARATUS AND NON-TRANSITORY COMPUTER READABLE MEDIUM

CROSS-REFERENCE TO RELATED APPLICATIONS

This application is based on and claims priority under 35 USC 119 from Japanese Patent Application No. 2017-167269 filed Aug. 31, 2017.

BACKGROUND

Technical Field

The present invention relates to an optical measuring apparatus and a non-transitory computer readable medium.

SUMMARY

According to an aspect of the invention, there is provided an optical measuring apparatus including first and second light-emitting elements that emit light and a controller. Upon detection of the presence of a body by light emitted from the first light-emitting element, the controller performs control so that the second light-emitting element will emit light with an amount for measuring the body.

BRIEF DESCRIPTION OF THE DRAWINGS

An exemplary embodiment of the present invention will be described in detail based on the following figures, wherein.

DETAILED DESCRIPTION

Figure 1:
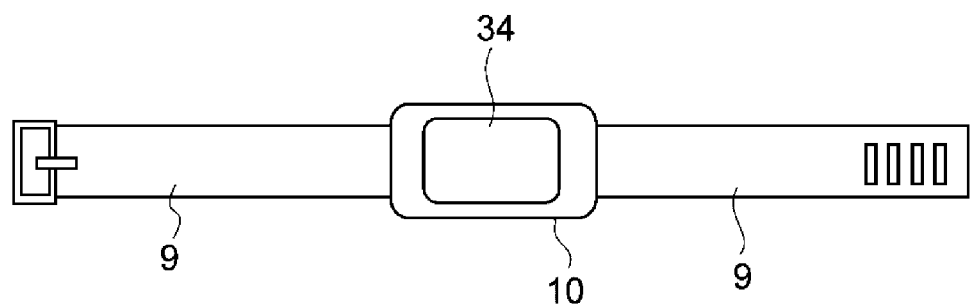
FIG. 1 is a schematic external view of the front side of an optical measuring apparatus.

An exemplary embodiment of the invention will be described below in detail with reference to the accompanying drawings. Elements having the same functions are designated by like reference numeral in the drawings and an explanation thereof will not be repeated.

Exemplary Embodiment

FIG. 1 is a schematic external view of an optical measuring apparatus 10.

The optical measuring apparatus 10 emits light to a body and analyzes light reflected by the body so as to measure various characteristics concerning the body (biological characteristics). Wristbands 9 are attached to both ends of the optical measuring apparatus 10 so that a user can wear the optical measuring apparatus 10 as a watch-type wearable terminal.

The optical measuring apparatus 10 also includes a display device 34, such as a liquid crystal display (LCD) or an organic electroluminescence (EL) display, and displays information concerning measured biological characteristics (biological information). For the sake of convenience, the surface of the optical measuring apparatus 10 on which the display device 34 is provided may be called the front side of the optical measuring apparatus 10.

Figure 2:
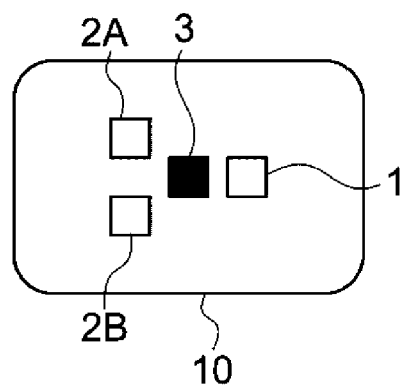
FIG. 2 is a schematic external view of the back side of the optical measuring apparatus.

FIG. 2 is a schematic external view illustrating an example of the surface of the optical measuring apparatus 10 that contacts a body. As shown in FIG. 2, on the surface of the optical measuring apparatus 10 that contacts a body, a laser emitting element 1, light-emitting diode (LED) elements 2A and 2B, and a light-receiving element 3 are disposed.

The laser emitting element 1 is a light-emitting element that emits laser light. Laser light is an example of coherent light that forms coherent light waves in phase with each other. The laser emitting element 1 may be a surface-emitting laser element or may be an edge-emitting laser element. Hereinafter, light in general including laser light will simply be called light, and if it is necessary to emphasize that light is laser light, light will be called laser light.

The LED elements 2A and 2B are light-emitting elements using LEDs. Instead of LEDs, the LED elements 2A and 2B may use organic light-emitting diodes (OLEDs).

The light-receiving element 3 receives light emitted from the laser emitting element 1 and the LED elements 2A and 2B and reflected by an object, and converts the amount of received light into a physical quantity representing the magnitude of light. In the exemplary embodiment, the light-receiving element 3 outputs a voltage in accordance with the amount of received light. However, the light-receiving element 3 may alternatively output a current in accordance with the amount of received light or change the resistance value.

The amount of light is a physical quantity that quantitatively represents light energy per unit time emitted from a light source. Luminous energy or luminous energy density, for example, is used as a physical quantity representing the amount of light. Luminous energy represents a total amount of luminous flux per unit time emitted from a light source in all directions. The luminous energy density represents the amount of luminous flux per unit area and per unit time emitted from a light source. Luminous energy represents the intensity of light, and the amount of light may be called the light intensity.

The positions of the laser emitting element 1, the LED elements 2A and 2B, and the light-receiving element 3 shown in FIG. 2 are only examples. The laser emitting element 1, the LED elements 2A and 2B, and the light-receiving element 3 may be arranged in any manner if the light-receiving element 3 is disposed to receive light reflected by a body irradiated with light from any of the laser emitting element 1 and the LED elements 2A and 2B.

If it is not necessary to distinguish the LED elements 2A and 2B from each other, they will collectively be called the LED element 2 or the LED elements 2.

A part of a body to be subjected to measurements of biological characteristics by the optical measuring apparatus 10 is not restricted to an arm, and may be any part of the body. The wristbands 9 may not necessarily be attached to the optical measuring apparatus 10. If a part of the body other than the arm is subjected to measurements of biological characteristics, a suitable mounting tool may be attached to the optical measuring apparatus 10 in accordance with the part of the body. For the sake of convenience, the surface of the optical measuring apparatus 10 that contacts a body may be called the back side of the optical measuring apparatus 10.

Figure 3:
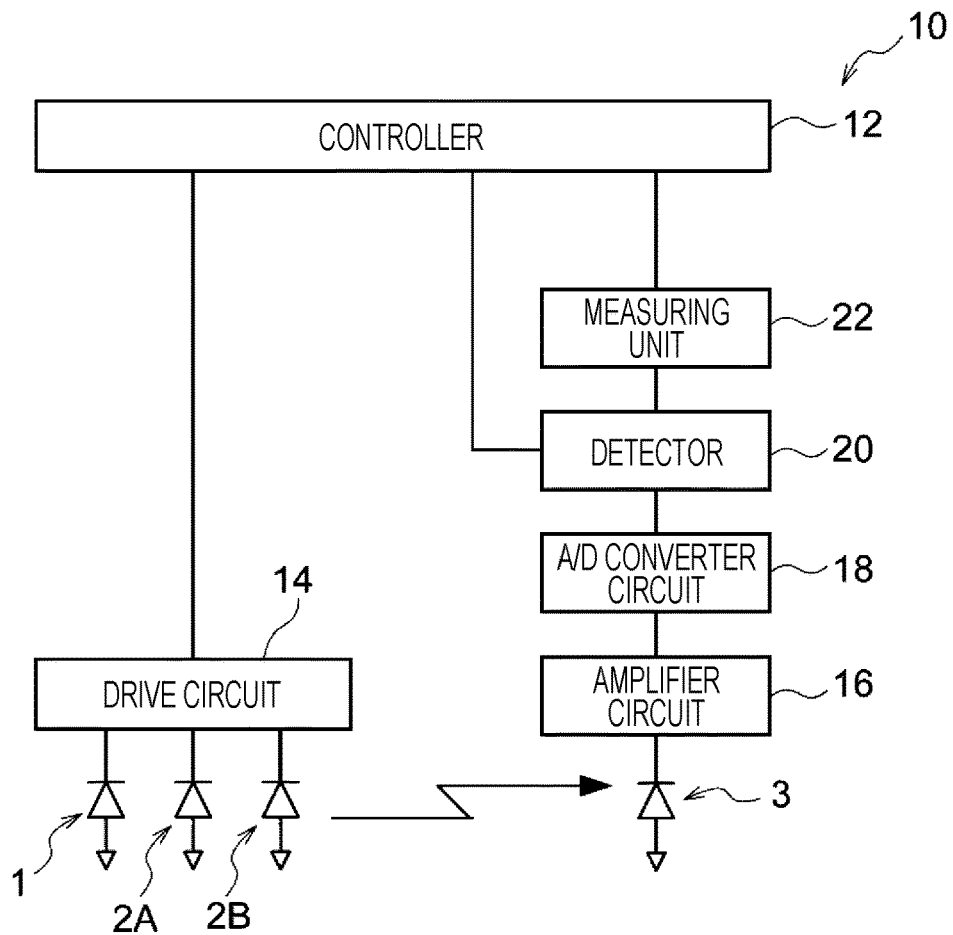
FIG. 3 illustrates an example of the configuration of the optical measuring apparatus.

FIG. 3 illustrates an example of the configuration of the optical measuring apparatus 10. As shown in FIG. 3, the optical measuring apparatus 10 includes the laser emitting element 1, the LED elements 2A and 2B, the light-receiving element 3, a controller 12, a drive circuit 14, an amplifier circuit 16, an analog-to-digital (A/D) converter circuit 18, a detector 20, and a measuring unit 22. With the configuration shown in FIG. 3, the optical measuring apparatus 10 measures a blood flow rate and percutaneous oxygen saturation (SpO2) (also called arterial blood oxygen saturation), which are examples of biological information representing biological characteristics.

In response to an instruction from the controller 12, the drive circuit 14 supplies drive power to drive the laser emitting element 1 and the LED elements 2A and 2B to emit light or stop emitting light.

The amplifier circuit 16 amplifies a voltage indicating the intensity of light received by the light-receiving element 3 to a voltage level included in an input voltage range of the A/D converter circuit 18.

The A/D converter circuit 18 receives the voltage amplified by the amplifier circuit 16, digitizes the intensity of light indicated by the voltage, and outputs the digitized light intensity to the detector 20.

The detector 20 performs fast Fourier transform (FFT) on a time change in the digitized light intensity per predetermined processing time (sampling time), thereby detecting a frequency distribution (spectral distribution) per frequency ω. The sampling time may be set to be several milliseconds to several hundreds of milliseconds, for example. In the exemplary embodiment, the sampling time is set to be 20 ms. The detector 20 outputs the detected spectral distribution and the time-series intensity of light received by the light-receiving element 3 to the measuring unit 22.

In response to an instruction from the controller 12, the measuring unit 22 measures a blood flow rate based on the spectral distribution detected by the detector 20, and also measures percutaneous oxygen saturation based on the intensity of light received by the light-receiving element 3. The detector 20 and the measuring unit 22 collaboratively detect a blood flow rate and percutaneous oxygen saturation, and are thus an example of a detector that detects biological information.

The controller 12 receives various instructions from a user, and also judges from the spectral distribution detected by the detector 20 whether the light-receiving element 3 has received light reflected by a blood vessel of a body. If the controller 12 judges that the light-receiving element 3 has received light reflected by a blood vessel of a body, it shifts the operating state of the optical measuring apparatus 10 from a standby mode to a measuring mode. More specifically, based on the spectral distribution detected by the detector 20 and the intensity of light received by the light-receiving element 3, the controller 12 drives the drive circuit 14 and the measuring unit 22 to start measuring a blood flow rate and percutaneous oxygen saturation, and also shifts the operating state of the optical measuring apparatus 10 from the standby mode to the measuring mode.

The standby mode is a state (standby state) in which neither of a blood flow rate nor percutaneous oxygen saturation is being measured. The measuring mode is a state (measuring state) in which at least one of a blood flow rate and percutaneous oxygen saturation is being measured.

That is, the standby mode is a state in which the optical measuring apparatus 10 has not yet shifted to the measuring mode or a state in which the optical measuring apparatus 10 has finished measurements. The standby mode thus refers to a state in which the intensity of light emitted from the laser emitting element 1 and the LED elements 2 is lower than that in the measuring mode and a state in which some functions of the optical measuring apparatus 10 are not functioning. The standby mode also refers to a state in which the optical measuring apparatus 10 is making preparations for shifting to the measuring state, such as a state in which the presence of a body is being detected. Such a state will be called a preparatory measuring state.

In contrast, the measuring mode is a mode in which biological characteristics are being measured for informing a user of measurement results. The measuring mode does not include the above-described preparatory measuring state.

The measuring principle of a blood flow rate in the optical measuring apparatus 10 will be discussed below. The measuring principle will be explained, assuming that the laser emitting element 1 is used to measure a blood flow rate. However, the LED element 2 may alternatively be used to measure a blood flow rate based on the same principle. The flow rate of blood flowing through a blood vessel may be measured by either one of light passing through the blood vessel and light reflected by the blood vessel, based on the same principle. A description will be given of a case in which a blood flow rate is measured by using light reflected by a blood vessel.

Figure 4:
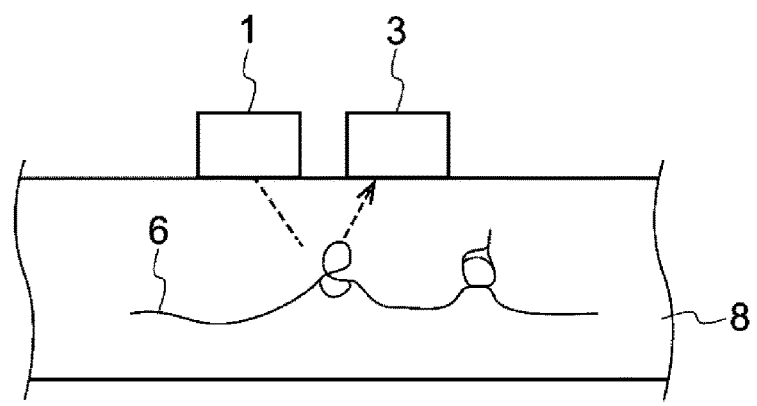
FIG. 4 illustrates an example of the arrangement of a light-emitting element and a light-receiving element.

FIG. 4 is a schematic view for explaining a state in which the back side of the optical measuring apparatus 10 is brought into contact with a body 8. In this state, the laser emitting element 1 and the light-receiving element 3 are disposed side by side on the surface of the body 8. The light-receiving element 3 receives light emitted from the laser emitting element 1 and reflected by a blood vessel 6 of the body 8.

Figure 5:
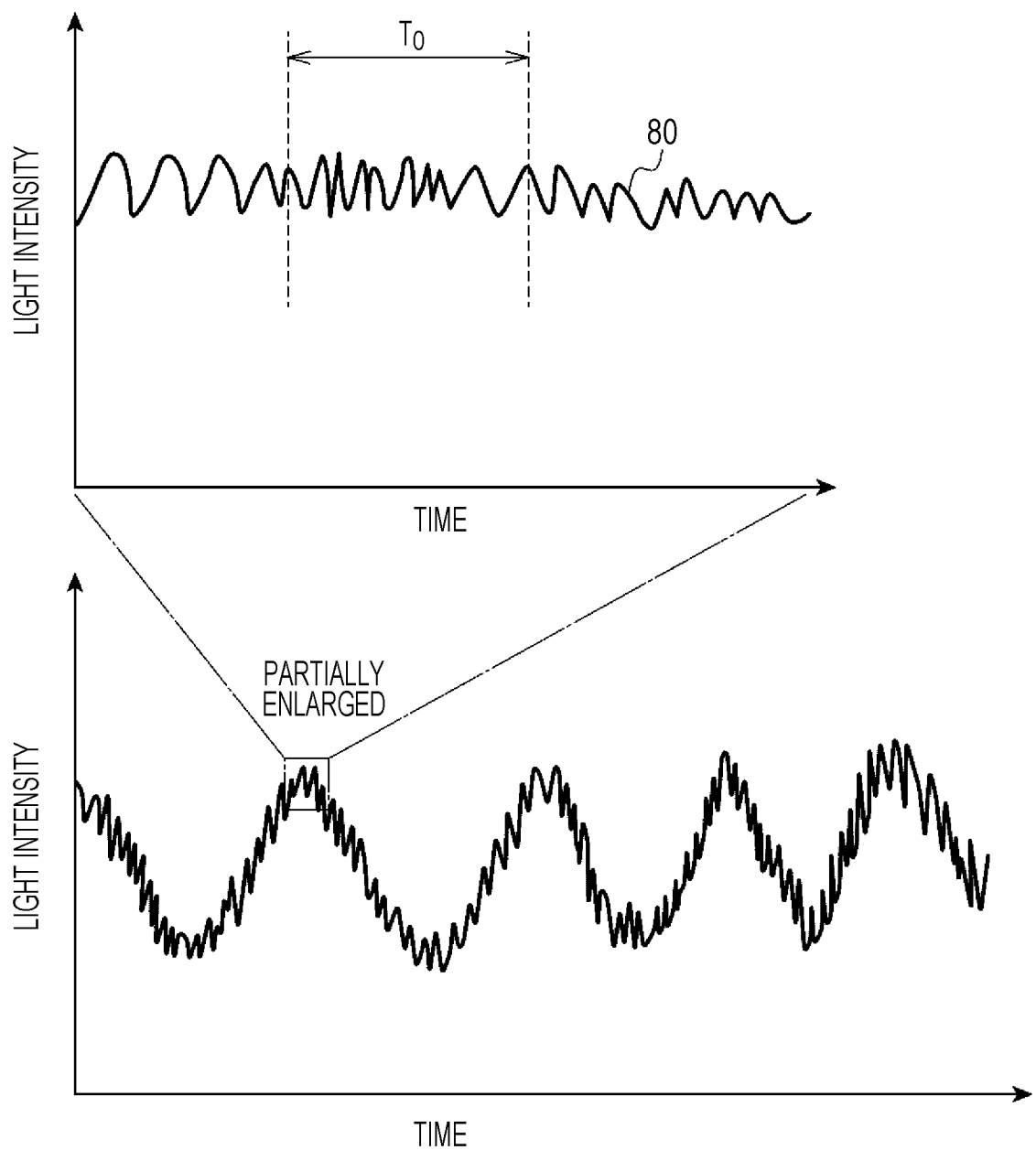
FIG. 5 shows graphs illustrating an example of a change in the intensity of light reflected by a body.

FIG. 5 shows graphs illustrating an example of the intensity of light reflected by the blood vessel 6 irradiated with light emitted from the laser emitting element 1 and received by the light-receiving element 3. In a graph on the upper section of FIG. 5, the horizontal axis indicates the time, and the vertical axis indicates output from the light-receiving element 3, that is, the intensity of light received by the light-receiving element 3. The intensity of light received by the light-receiving element 3 may simply be called the light intensity.

As shown in FIG. 5, the light intensity changes over time. This may be caused by the influence of three optical phenomena resulting from the irradiation of the body 8 including the blood vessel 6.

A first optical phenomenon is a variation in light absorption in the blood vessel 6. The volume of blood in the blood vessel 6 is changing because of pulsation. This may vary light absorption in the blood vessel 6. Blood contains blood cells, such as red blood cells, and blood cells move within the blood vessel 6 such as a blood capillary. Changing of the blood volume may increase or decrease blood cells moving within the blood vessel 6. This may influence the intensity of light received by the light-receiving element 3.

A second optical phenomenon is the occurrence of a Doppler shift.

Figure 6:
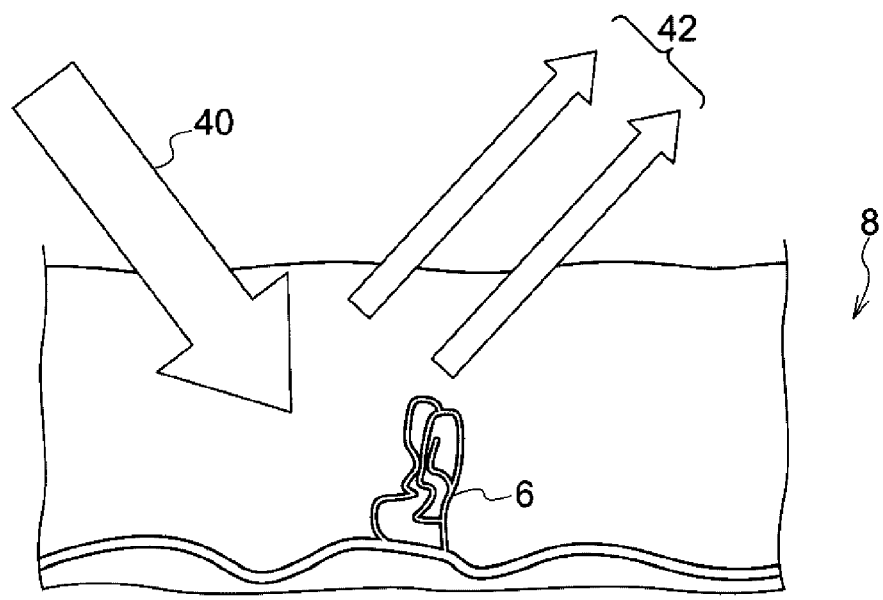
FIG. 6 is a schematic view for explaining the occurrence of a Doppler shift when light is applied to a blood vessel.

As shown in FIG. 6, when coherent light 40, such as laser light, having a frequency $\omega_0$ is applied from the laser emitting element 1 to a region including the blood vessel 6, it is scattered by blood cells moving within the blood vessel 6. At this time, a Doppler shift having a difference frequency $\Delta\omega_0$, which is determined by the moving velocity of the blood cells, occurs in scattered light 42 generated as a result of the laser light being scattered by the blood cells. In contrast, the frequency of scattered light 42 generated as a result of the laser light being scattered by tissue (stationary tissue) such as the skin, which does not contain moving elements such as blood cells, is maintained at the same frequency as the frequency $\omega_0$ of the laser light. The frequency $\omega_0+\Delta\omega_0$ of the laser light scattered by the blood vessel 6 and the frequency $\omega_0$ of the laser light scattered by the stationary tissue interfere with each other. A beat signal having a difference frequency $\Delta\omega_0$ is thus observed at the light-receiving element 3. As a result, the intensity of light received by the light-receiving element 3 changes over time. The difference frequency $\Delta\omega_0$ of the beat signal is determined by the moving velocity of the blood cells, and is contained in a range at a maximum of several dozens of kilohertz.

A third optical phenomenon is the generation of speckles.

Figure 7:
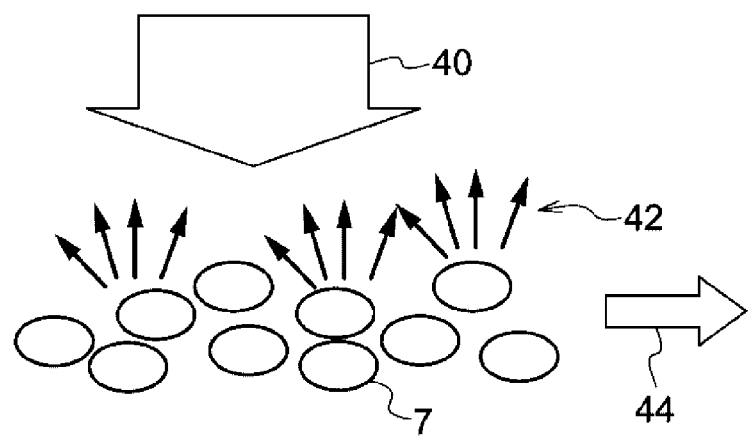
FIG. 7 is a schematic view for explaining the generation of speckles when light is applied to a blood vessel.

As shown in FIG. 7, coherent light 40 such as laser light is applied to blood cells 7, such as red blood cells, moving within the blood vessel 6 in a direction indicated by an arrow 44. Then, the coherent light 40 strikes the blood cells 7 and is scattered in various directions. The scattered light waves are out of phase with each other and thus randomly interfere with each other. Because of the random interference of light waves, random speckles are observed in the resulting light intensity distribution. Such a light intensity distribution pattern is called a speckle pattern.

The blood cells 7 move within the blood vessel 6. Thus, the scattering state of light striking the blood cells 7 varies over time, and the speckle pattern also varies over time. As a result, the intensity of light received by the light-receiving element 3 changes over time.

Figure 8:
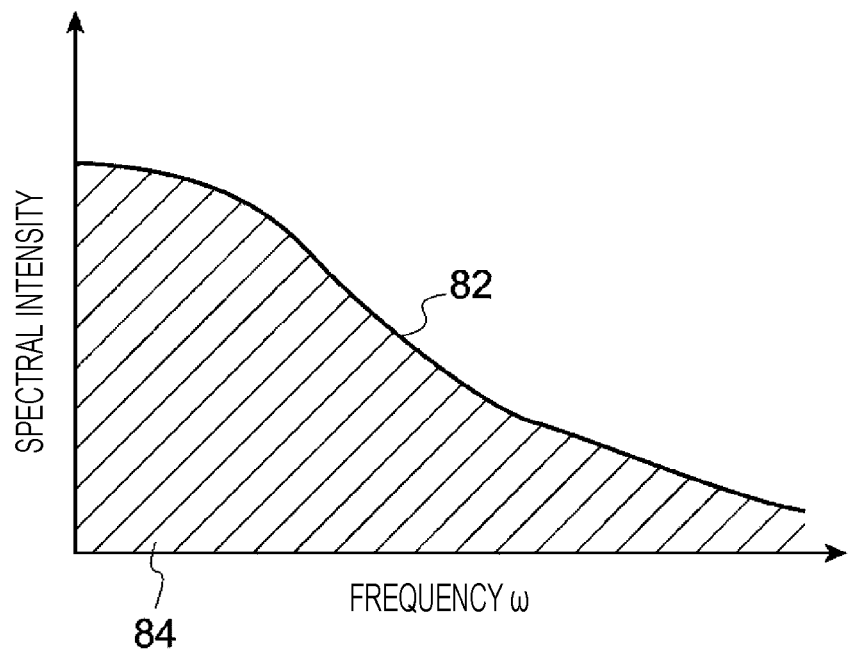
FIG. 8 is a graph illustrating an example of a spectral distribution of light reflected by a body.

When the light-receiving element 3 has received light having intensity which changes over time, the following processing is executed on data indicating the light intensity. A portion of data in a range of predetermined a unit time $T_0$ is extracted, and FFT processing, for example, is executed on the extracted portion of data, thereby obtaining a spectral distribution per frequency $\omega$. FIG. 8 is a graph illustrating an example of a spectral distribution 82 per frequency w within the time unit $T_0$ of light reflected by the blood vessel 6. In the graph of FIG. 8, the horizontal axis indicates the frequency $\omega$, and the vertical axis indicates the magnitude of frequency components, that is, the spectral intensity, with respect to the frequency $\omega$. The spectral distribution 82 of light reflected by the blood vessel 6 is 0 hertz to several dozens of kilohertz, and more specifically, in a range of 0 Hz to about 20 kHz.

The blood volume is proportional to a value obtained by standardizing the area of a hatched portion 84 by the total amount of light. The hatched portion 84 is a portion surrounded by the spectral distribution 82 and the horizontal and vertical axes. The velocity of blood flowing through the blood vessel 6 (blood flow velocity) is proportional to the frequency average of the spectral distribution 82. That is, the blood flow velocity is proportional to a value calculated as follows. The product of the frequency $\omega$ and the spectral intensity at the frequency $\omega$ is integrated with respect to the frequency $\omega$. The resulting integrated value is then divided by the area of the hatched portion 84. The blood flow velocity is proportional to the resulting divided value.

The blood flow rate is expressed by the product of the blood volume and the blood flow velocity, and is thus calculated from these two elements.

Figure 9:
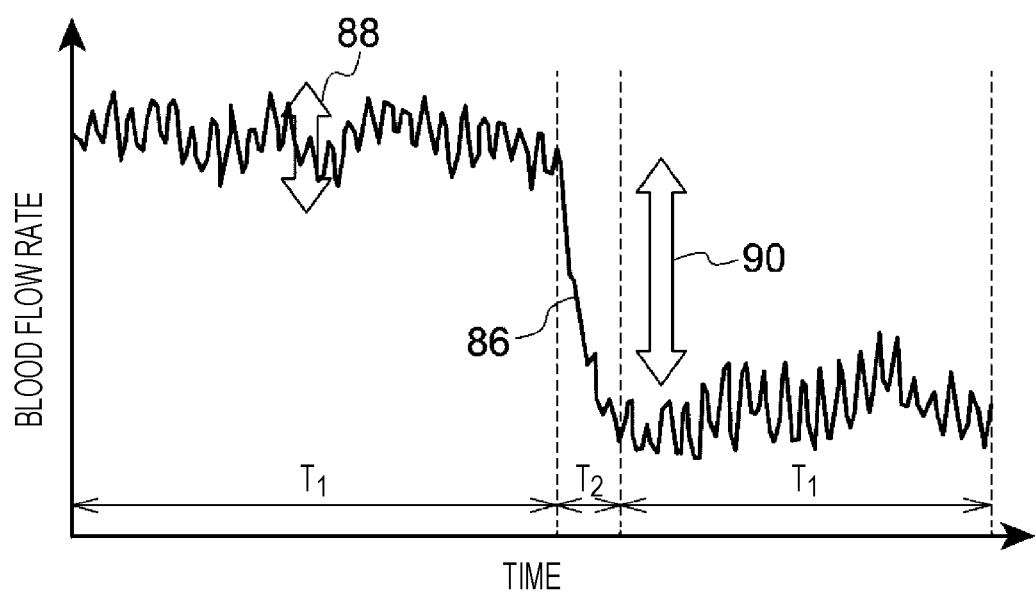
FIG. 9 is a graph illustrating an example of a variation in the blood flow rate.

FIG. 9 is a graph illustrating an example of a variation in the blood flow rate measured as described above per unit time $T_0$. In the graph of FIG. 9, the horizontal axis indicates the time, and the vertical axis indicates the blood flow rate.

As shown in FIG. 9, the blood flow rate varies over time. The pattern of a variation in the blood flow rate can be divided into two types. For example, a range of a variation 90 in the blood flow rate during an interval $T_2$ is greater than that of a variation 88 during an interval $T_1$. The reason for this may be that, while a variation in the blood flow rate during the interval $T_1$ is caused principally by pulsation, a variation in the blood flow rate during the interval $T_2$ is caused by vascular congestion, for example.

The measuring principle of percutaneous oxygen saturation in the optical measuring apparatus 10 will be discussed below. The measuring principle will be explained, assuming that the LED elements 2A and 2B are used to measure the percutaneous oxygen saturation. However, the LED element 2 and the laser emitting element 1 or plural laser emitting elements 1 may alternatively be used to measure the percutaneous oxygen saturation, based on the same principle.

The percutaneous oxygen saturation is an index for representing how much of hemoglobin contained in blood is bound to oxygen. As the percutaneous oxygen saturation is lower, a symptom, such as anemia, is more likely to occur.

Figure 10:
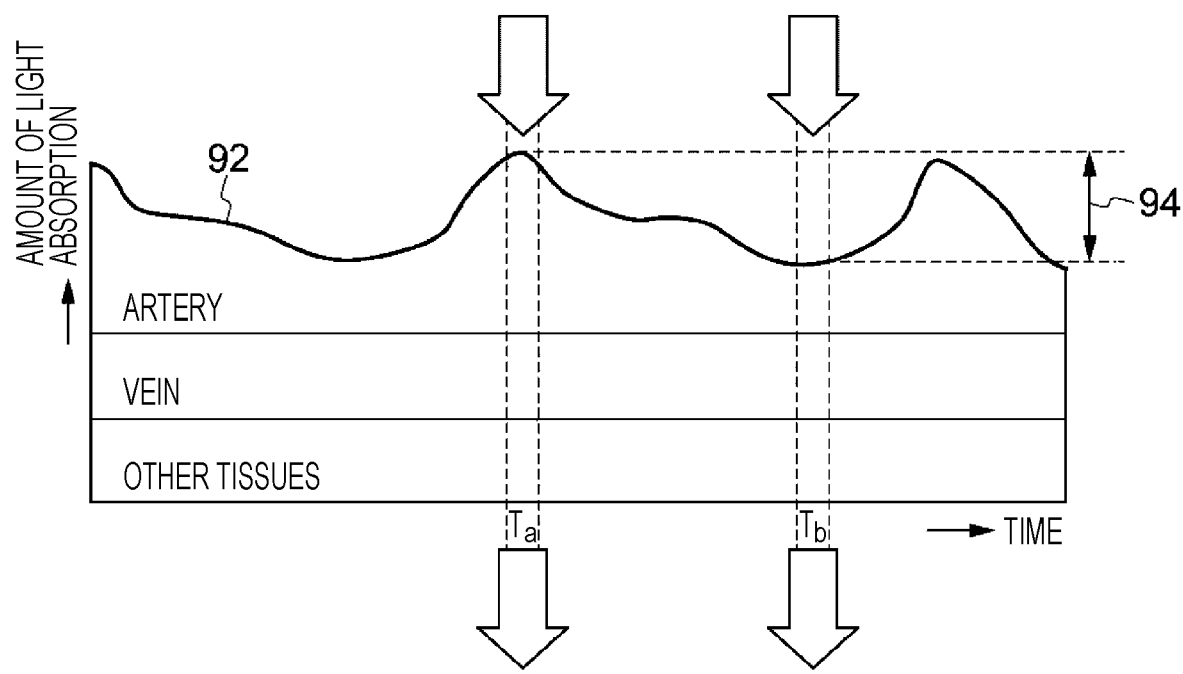
FIG. 10 is a graph illustrating a variation in the amount of light absorbed in a body.

FIG. 10 is a conceptual diagram illustrating a variation in the amount of light absorbed in the body 8, which may also be called the amount of light absorption. As shown in FIG. 10, the amount of light absorbed in the body 8 is likely to change over time.

The breakdown of a variation in the amount of light absorption illustrated in FIG. 10 shows that a variation in the amount of light absorption occurs principally by an artery, while that by a vein and other tissues including stationary tissue is almost negligible. The reason for this is as follows.

Blood pumped out from a heart moves through an artery with pulse waves, and thus, the artery expands and contracts in a cross section over time, and the thickness of the artery changes accordingly. In FIG. 10, a range indicated by an arrow 94 is a variation in the amount of light absorption according to a change in the thickness of the artery.

If the light intensity at time $t_a$ in FIG. 10 is indicated by $I_a$ and that at time $t_b$ in FIG. 10 is indicated by $I_b$, a variation $\Delta A$ in the amount of light absorption due to a change in the thickness of the artery is expressed by equation (1).

$$\Delta A = \ln(I_b/I_a) \quad (1)$$

Hemoglobin in blood flowing through an artery bound to oxygen (oxyhemoglobin) is known to be likely to absorb infrared (IR) light, while hemoglobin which is not bound to oxygen (deoxyhemoglobin) is known to be likely to absorb red light. It is also known that the percutaneous oxygen saturation is proportional to the ratio of a variation $\Delta A$ in the amount of light absorption with respect to a certain wavelength to that with respect to another wavelength.

If IR light and red light are used, a difference in the amount of light absorption between oxyhemoglobin and deoxyhemoglobin is likely to be larger than that when a combination of other light wavelengths is used. By using IR light and red light, the ratio of a variation $\Delta A_{Red}$ in the amount of light absorption in the body 8 irradiated with red light to a variation $\Delta A_{IR}$ in the amount of light absorption in the body 8 irradiated with IR light is calculated. The percutaneous oxygen saturation S is calculated by equation (2):

$$S = k(\Delta A_{Red}/\Delta A_{IR}) \quad (2)$$

where k is a proportionality constant.

In calculating the percutaneous oxygen saturation, light emission periods of the LED elements 2A and 2B which emit different wavelengths of light may overlap each other. More specifically, the light emission period of the LED element 2A which emits red light and that of the LED element 2B which emits IR light may overlap each other. It is more desirable, however, that the two light emission periods do not overlap. The light-receiving element 3 receives light reflected by the body 8 irradiated with red light from the LED element 2A and that irradiated with IR light from the LED element 2B. Based on the intensity of light received by the light-receiving element 3 at one time point and that at another time point, equations (1) and (2) or known equations deformed from equations (1) and (2) are calculated, so that the percutaneous oxygen saturation can be measured.

For example, equation (1) may be expanded to equation (3) to express a variation $\Delta A$ in the amount of light absorption.

$$\Delta A = \ln(I_b) - \ln(I_a) \quad (3)$$

Equation (1) may be deformed into equation (4).

$$\Delta A = \ln(I_b/I_a) = \ln(1 + (I_b - I_a)) \quad (4)$$

Usually, $(I_b - I_a) \ll I_a$, and thus, $\ln(I_b/I_a) \approx (I_b - I_a)/I_a$ is established. Accordingly, instead of equation (1), equation (5) may be used.

$$\Delta A \approx (I_b - I_a)/I_a \quad (5)$$

The configuration of the major parts of the electrical system of the optical measuring apparatus 10 will be described below with reference to FIG. 11.

Figure 11:
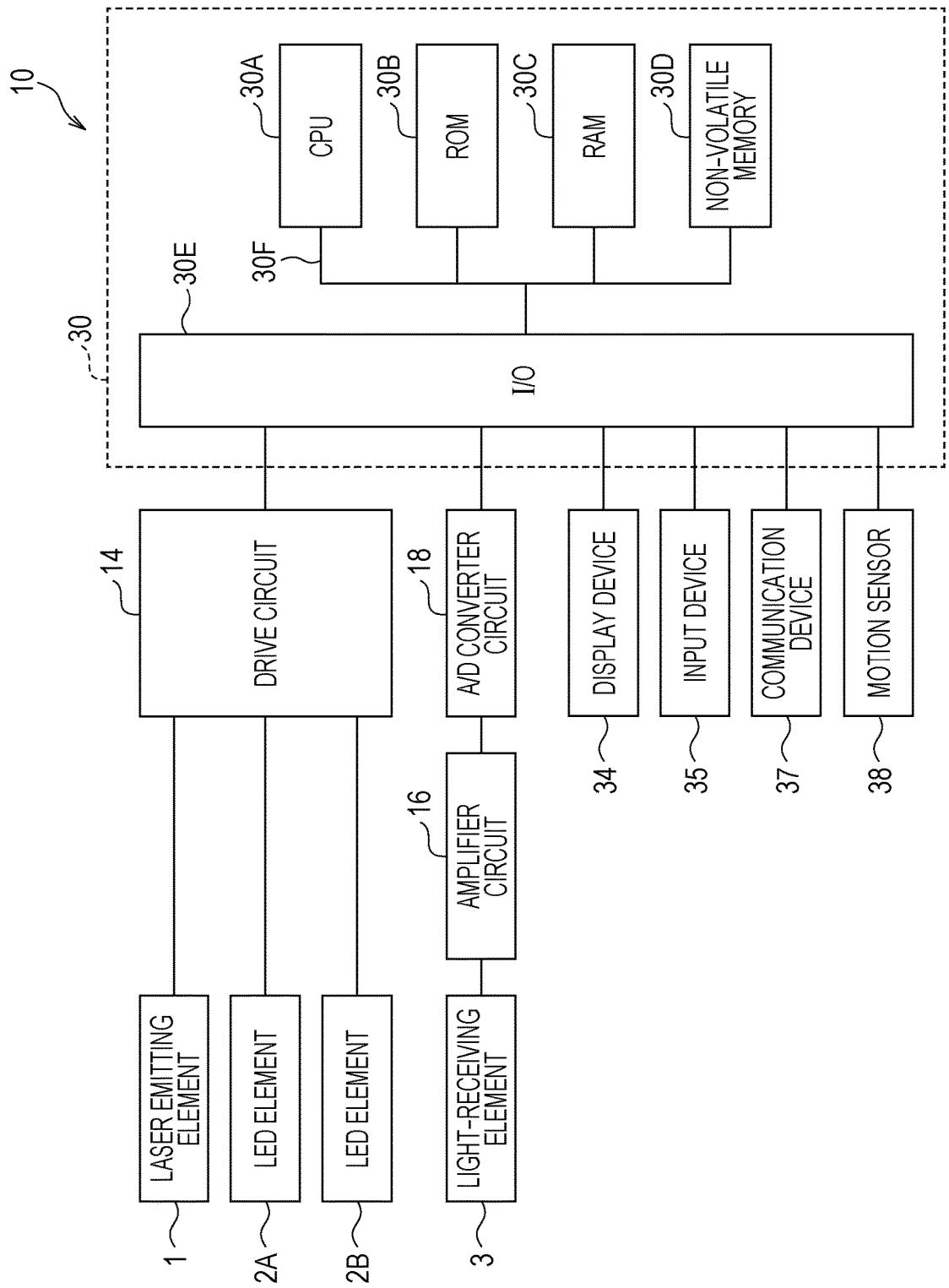
FIG. 11 is a block diagram illustrating an example of the configuration of the major parts of the electrical system of the optical measuring apparatus.

As shown in FIG. 11, the controller 12, the detector 20, and the measuring unit 22 of the optical measuring apparatus 10 are constituted by a computer 30. The computer 30 includes a central processing unit (CPU) 30A, a read only memory (ROM) 30B, a random access memory (RAM) 30C, a non-volatile memory 30D, and an input/output interface (I/O) 30E. The CPU 30A, the ROM 30B, the RAM 30C, the non-volatile memory 30D, and the I/O 30E are connected to one another via a bus 30F.

The drive circuit 14, the A/D converter circuit 18, the display device 34, an input device 35, a communication device 37, and a motion sensor 38 are connected to the I/O 30E. The laser emitting element 1 and the LED elements 2A and 2B are connected to the drive circuit 14. The light-receiving element 3 is connected to the A/D converter circuit 18 via the amplifier circuit 16. The CPU 30A is an example of a detector and a controller.

The display device 34 is a display that visually supply information concerning the start and the end of measurements of biological information and measured biological information, such as measurement results, to a user. The display device 34 may be constituted by light-emitting elements, such as LEDs, and biological information may be supplied to a user by changing the number, configuration, and color of LEDs to be turned ON.

The input device 35 is an example of a receiver that receives an instruction from a user for the optical measuring apparatus 10. Buttons and a touchscreen, for example, are used for the input device 35. In the example of the optical measuring apparatus 10 shown in FIG. 1, a touchscreen is superposed on the display device 34 and receives an instruction from a user. A microphone which converts a voice instruction from a user to an electric signal is also an example of the input device 35.

The communication device 37 has a communication protocol so as connect to a communication network, such as the Internet, and to send and receive data to and from an external device connected to the communication network. The optical measuring apparatus 10 sends measured biological information to an external device or receives an instruction from an external device via the communication device 37. The communication network connected to the communication device 37 may be either one of a wired medium and a wireless medium.

The motion sensor 38 is a sensor which detects physical motion (physical operation) in the optical measuring apparatus 10, and may be an acceleration sensor or a gyroscope.

The devices connected to the I/O 30E shown in FIG. 11 are only examples. Another device may be connected to the I/O 30E. For example, a speaker which supplies information concerning the start and the end of measurements of biological information and measured biological information to a user in sound may be connected to the I/O 30E.

It is assumed, for example, that the center wavelength of light emitted from the LED element 2A is a wavelength contained in the red light region, and the center wavelength of light emitted from the LED element 2B is a wavelength contained in the IR light region. As discussed above, oxyhemoglobin is more likely to absorb IR light, while deoxyhemoglobin is more likely to absorb red light. Thus, by setting the center wavelength of light emitted from the LED element 2A to be contained in the red light region and that emitted from the LED element 2B to be contained in the IR light region, the precision in measuring the percutaneous oxygen saturation is improved to a higher level than when plural LED elements which emit light having the same center wavelength are used.

The center wavelength of light emitted from the laser emitting element 1 is set to be about 850 nm. However, this is only an example, and the center wavelength of the laser emitting element 1 may be set to be a different value.

Figure 12:
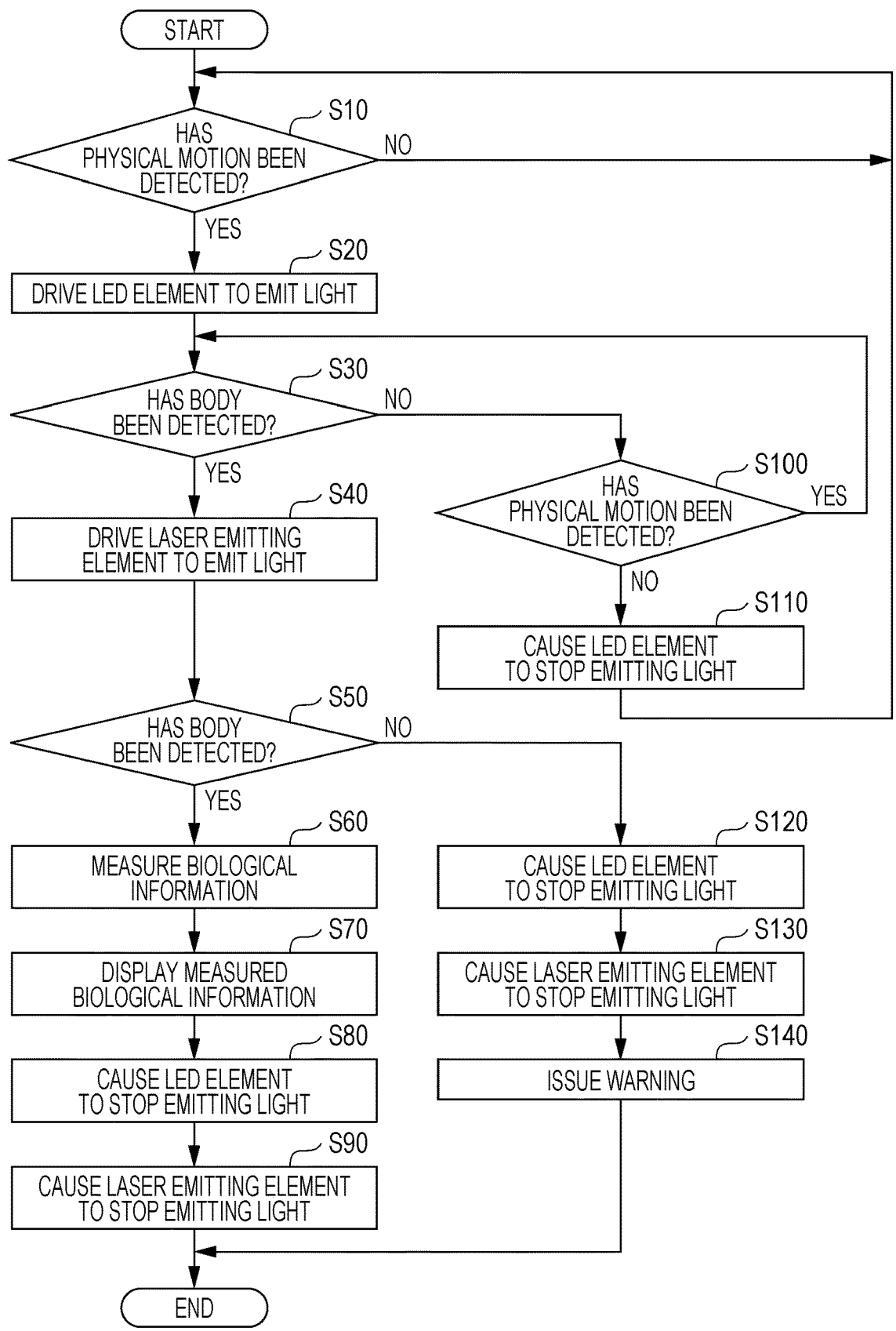
FIG. 12 is a flowchart illustrating an example of optical measuring processing.

The operation of the optical measuring apparatus 10 will be described below. FIG. 12 is a flowchart illustrating an example of optical measuring processing executed by the CPU 30A when the optical measuring apparatus 10 is powered ON.

An optical measuring program for executing optical measuring processing is stored in the ROM 30B. When the optical measuring apparatus 10 is powered ON, the CPU 30A reads the optical measuring program from the ROM 30B and executes it. It is assumed that, at the start of executing the optical measuring program, none of the laser emitting element 1 and the LED elements 2A and 2B emit light. It is also assumed that the amount of light for measuring a body (luminous flux $L_{1a}$) to be emitted from the laser emitting element 1 in the measuring mode is set to be larger than that (luminous flux $L_{2a}$) to be emitted from the LED elements 2A and 2B in the measuring mode.

In step S10, the CPU 30A obtains an output value of the motion sensor 38 and judges whether physical motion has been detected in the optical measuring apparatus 10. More specifically, if the output value of the motion sensor 38 is equal to or higher than a motion threshold, the CPU 30A judges that physical motion has been detected in the optical measuring apparatus 10. The motion threshold may be found by experiment using an actual product of the optical measuring apparatus 10 or by computer simulations based on the design specifications of the optical measuring apparatus 10, and may be stored in the non-volatile memory 30D.

If the result of step S10 is NO, it is likely that a user has not touched the optical measuring apparatus 10. The CPU 30A thus repeats step S10 to monitor the output value of the motion sensor 38 until the user touches the optical measuring apparatus 10.

If the result of step S10 is YES, it is likely that the user has held the optical measuring apparatus 10 and is starting to wear it. The CPU 30A then determines that the user is starting to measure biological information and then proceeds to step S20. That is, the user does not actually have to provide an instruction to measure biological information, and instead, the user merely holds the optical measuring apparatus 10, and then, preparations for measuring biological information are automatically started.

In step S10, the CPU 30A detects physical motion in the optical measuring apparatus 10 to judge whether an instruction to start measuring biological information has been provided. Instead of executing step S10, upon receiving an instruction to start measuring biological information from a user via the input device 35, the CPU 30A may proceed to step S20. Even if physical motion is detected in the optical measuring apparatus 10, it is possible that the user has simply moved the optical measuring apparatus 10 without intending to measure biological information. By receiving an instruction to start measuring biological information from a user, preparations for measurements can be started at a more precise timing.

Instead of executing step S10, after the optical measuring apparatus 10 is powered ON, step S20 may be executed at a predetermined interval (ten minutes, for example). In this case, the motion sensor 38 is not necessary, and the cost of the optical measuring apparatus 10 can be reduced.

In step S20, the CPU 30A controls the drive circuit 14 so that the one of the LED elements 2A and 2B will emit light in a predetermined cycle. Causing only one of the LED elements 2A and 2B to emit light can reduce power consumed in the optical measuring apparatus 10 in the standby mode, compared with when both of the LED elements 2A and 2B emit light. The following description will be given, assuming that the LED element 2A is driven to emit light.

The drive circuit 14 drives the LED element 2A to emit light with a light emission pattern in a 200 ms cycle in which the LED element 2A emits light for 20 ms and stops emitting light for 180 ms. However, this light emission pattern is only an example. The drive circuit 14 may drive the LED element 2A to emit light with another light emission pattern.

As discussed above, the amount of light is a physical quantity represented by the product of luminous flux and a time. Even if luminous flux of light emitted from the LED element 2A is fixed at the same value, the amount of light becomes different by changing the light emission pattern of the LED element 2A. For the sake of description, the light emission patterns of the laser emitting element 1 and the LED elements 2A and 2B are set to be the same pattern, and luminous flux of light emitted from each of the laser emitting element 1 and the LED element 2 is adjusted, thereby controlling the amount of light emitted from each of the laser emitting element 1 and the LED element 2. However, luminous flux of light emitted from the laser emitting element 1 and the LED elements 2A and 2B may be set to be the same, and the light emission patterns of the laser emitting element 1 and the LED element 2 may be adjusted so as to control the amount of light emitted from each of the laser emitting element 1 and the LED element 2. Alternatively, by adjusting luminous flux of light emitted from each of the laser emitting element 1 and the LED elements 2A and 2B and the light emission patterns thereof, the amount of light emitted from each of the laser emitting element 1 and the LED elements 2A and 2B may be controlled.

Luminous flux of light emitted from the LED element 2A in step S20 is adjusted to luminous flux $L_{2b}$ corresponding to the amount of light for detecting a body and is restricted to be less than luminous flux $L_{2a}$. Luminous flux $L_{2a}$ corresponds to the amount of light for measuring a body emitted from the LED element 2A in the measuring mode.

Driving the LED element 2A to emit light refers to, not only that luminous flux of light emitted from the LED element 2A is raised from 0 lumens to a value exceeding 0 lumens, but also that luminous flux $L_b$ exceeding 0 lumens is raised to luminous flux $L_a$ ($L_b<L_a$). This concept of light emission also applies to the driving of the laser emitting element 1.

In step S30, the CPU 30A obtains the intensity of light received by the light-receiving element 3 for a predetermined body detection period (ten seconds, for example) from the A/D converter circuit 18. Based on the characteristics of the intensity of light received by the light-receiving element 3, the CPU 30A determines whether the body 8 has been detected. As expressed in equation (1), a variation ΔA in the amount of light absorption varies due to a change in the thickness of an artery. If a time change in the intensity of light received by the light-receiving element 3 indicates a time change in pulse waves, the CPU 30A determines that the body 8 has been detected.

If the body 8 has not been detected during the body detection period, various situations may be considered. For example, the user may still be trying to wear the optical measuring apparatus 10 on the arm or may have placed the optical measuring apparatus 10 on a desk without wearing it.

The CPU 30A thus proceeds to step S100 to execute the same processing as step S10 to judge whether physical motion has been detected in the optical measuring apparatus 10. If physical motion has been detected, the user may still be holding the optical measuring apparatus 10 in hand and trying to wear it on the arm. The CPU 30A thus proceeds to step S30 to judge again whether the body 8 has been detected.

If physical motion has not been detected in step S100, the user may have held the optical measuring apparatus 10 but placed it on a desk without wearing it. The CPU 30A thus proceeds to step S110.

In step S110, the CPU 30A causes the LED element 2A to stop emitting light because light from the optical measuring apparatus 10 may be applied to objects other than the user. This can reduce the possibility that someone other than the user will accidentally be irradiated with light from the optical measuring apparatus 10. Then, the CPU 30A returns to step S10 to monitor the output value of the motion sensor 38.

In step S110, instead of causing the LED element 2A to stop emitting light, the amount of light emitted from the LED element 2A may be reduced to such a degree not to make people uncomfortable. Such a reduced amount of light may also be called a standby light amount.

If the body 8 has been detected during the body detection period in step S30, the CPU 30A proceeds to step S40.

In step S40, the CPU 30A controls the drive circuit 14 so that the laser emitting element 1 will emit light with a predetermined light emission pattern. In this case, luminous flux of light emitted from the laser emitting element 1 is adjusted to luminous flux $L_{1b}$ corresponding to the amount of light for detecting a body and is restricted to be less than luminous flux $L_{1a}$. Luminous $L_{1a}$ corresponds to the amount of light for measuring a body emitted from the laser emitting element 1 in the measuring mode. The CPU 30A adjusts the phase of the light emission pattern of the laser emitting element 1 and that of the LED element 2A, that is, the start timing of light emission of the laser emitting element 1 and that of the LED element 2A, so that the light emission period of the laser emitting element 1 and that of the LED element 2A will not overlap each other.

In step S50, based on light emitted from the laser emitting element 1 and received by the light-receiving element 3, the CPU 30A judges whether the body 8 has been detected.

More specifically, the CPU 30A executes FFT processing on a time change in the intensity of light emitted from the laser emitting element 1 digitized by the A/D converter circuit 18, thereby detecting a spectral intensity per frequency w as the spectral distribution 82. The CPU 30A then judges whether the spectral intensity at a predetermined frequency (reference frequency) exceeds a predetermined threshold, which is preset as a value obtained when light is applied from the laser emitting element 1 to the body 8. If the spectral intensity at the reference frequency exceeds the predetermined threshold, the CPU 30A determines that the body 8 has been detected.

The light emission pattern of the laser emitting element 1 and that of the LED element 2A are made out of phase with each other in step S40, so that the interference of light from the laser emitting element 1 and that from the LED element 2A can be reduced. This enhances the precision in detecting the body 8 by using light from the laser emitting element 1.

If it is found in step S50 that the body 8 has been detected, the CPU 30A proceeds to step S60.

As the body 8 has been detected by light from the LED element 2A and that from the laser emitting element 1, it is most probably that the user has worn the optical measuring apparatus 10 on the arm. In step S60, the CPU 30A thus shifts the optical measuring apparatus 10 from the standby mode to the measuring mode to measure a blood flow rate and percutaneous oxygen saturation of the user.

More specifically, the CPU 30A controls the drive circuit 14 so that luminous flux of light emitted from the LED element 2A will be raised from $L_{2b}$ to $L_{2a}$ ($L_{2b}<L_{2a}$), that is, the amount of light emitted from the LED element 2A for detecting a body will be raised to that for measuring a body. The CPU 30A also controls the drive circuit 14 so that luminous flux of light emitted from the laser emitting element 1 will be raised from $L_{1b}$ to $L_{1a}$ ($L_{1b}<L_{1a}$), that is, the amount of light emitted from the laser emitting element 1 for detecting a body will be raised to that for measuring a body. The CPU 30A also controls the drive circuit 14 so that the LED element 2B will emit light with an amount for measuring a body. Luminous flux of light emitted from the LED element 2B is set to be $L_{2a}$, which is the same as that from the LED element 2A. However, luminous flux of the LED element 2B may be other than $L_{2a}$.

The CPU 30A adjusts the phase of the light emission pattern so that the light emission period of the LED element 2B will not overlap each of that of the laser emitting element 1 and that of the LED element 2A. This can reduce the interference of light from the laser emitting element 1, that from the LED element 2A, and that from the LED element 2B, thereby enhancing the precision in measuring biological information.

The CPU 30A executes FFT processing on a time change in the intensity of light emitted from the laser emitting element 1 digitized by the A/D converter circuit 18, thereby detecting the spectral distribution 82 per frequency w. By using the spectral distribution 82, the CPU 30A calculates the blood volume and the blood flow velocity according to the above-described method, and then finds the blood flow rate from the product of the blood volume and the blood flow velocity. The CPU 30A stores the measurement results in the RAM 30C, for example.

The CPU 30A then calculates the percutaneous oxygen saturation S according to equations (1) and (2) by using the intensity of light received by the light-receiving element 3 for the light emission period of the LED element 2A and that for the light emission period of the LED element 2B.

In step S70, the CPU 30A displays on the display device 34 the blood flow rate and percutaneous oxygen saturation of the user measured in step S60 in a form that is recognizable by the user, such as in numeric values, graphs, or characters. In addition to displaying the measurement results on the display device 34, the CPU 30A may also send the measurement results via the communication device 37 to an external device connected to a communication network and display and store the measurement results on the external device.

The CPU 30A has finished measuring the blood flow rate and percutaneous oxygen saturation. In step S80, the CPU 30A thus controls the drive circuit 14 so that the LED elements 2A and 2B will stop emitting light.

In step S90, the CPU 30A controls the drive circuit 14 so that the laser emitting element 1 will stop emitting light. In this case, no restriction is imposed on which one of the laser emitting element 1 and the LED element 2 stops emitting light first. The laser emitting element 1 may stop emitting light first, and then, the LED element 2 may stop emitting light.

The optical measuring apparatus 10 is then switched from the measuring mode to the standby mode to complete optical measuring processing shown in FIG. 12.

If the result of step S50 is NO, that is, if the body 8 has not been detected by laser light, the CPU 30A proceeds to step S120.

Even when the body 8 has been detected by light emitted from the LED element 2A in step S30, if the body 8 has not been detected by light emitted from the laser emitting element 1, it is possible that an error has occurred in detecting the body 8 by using light emitted from the LED element 2. Even if biological information is measured in a state in which it is not known whether the user has worn the optical measuring apparatus 10 on the arm, correct measurement results may not been obtained, thereby discontinuing measuring biological information.

In step S120, the CPU 30A controls the drive circuit 14 so that the LED elements 2A and 2B will stop emitting light.

In step S130, the CPU 30A controls the drive circuit 14 so that the laser emitting element 1 will stop emitting light. In this case, no restriction is imposed on which one of the laser emitting element 1 and the LED element 2 stops emitting light first. The laser emitting element 1 may stop emitting light first, and then, the LED element 2 may stop emitting light.

In step S140, the CPU 30A issues a warning to inform the user of a failure to detect the body 8. In this case, a warning may be issued in any manner. For example, a warning message may be displayed on the display device 34. If the optical measuring apparatus 10 has a speaker, a warning may be issued as sound. If the optical measuring apparatus 10 has a vibrator that vibrates based on a voltage, a warning may be issued as vibration.

After step S140, the optical measuring apparatus 10 is switched from the measuring mode to the standby mode to complete optical measuring processing shown in FIG. 12.

Figure 13:
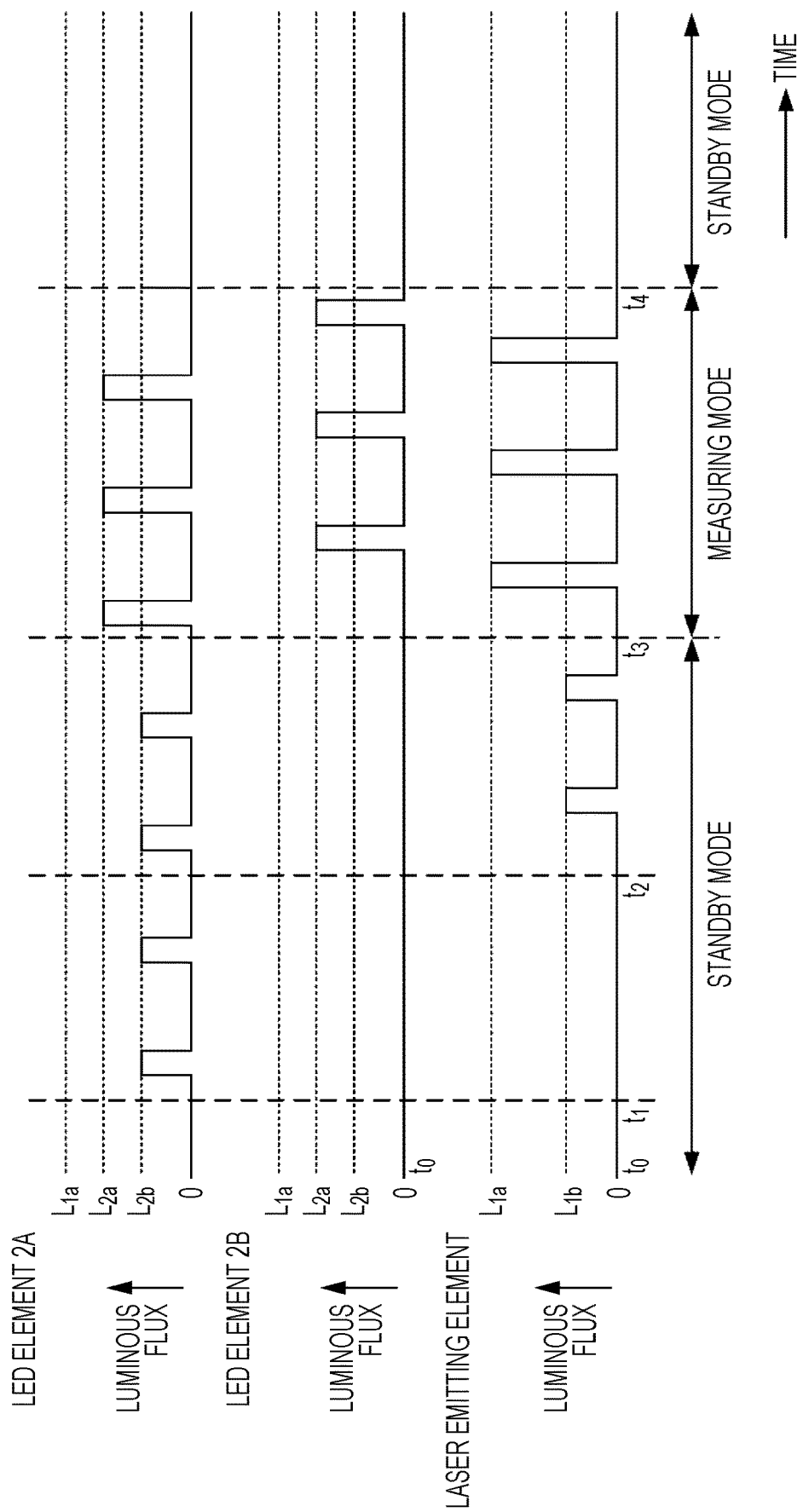
FIG. 13 is a timing chart illustrating an example of a light emission state of each of a laser emitting element and light-emitting diode (LED) elements according to optical measuring processing shown in FIG. 12.

FIG. 13 is a timing chart illustrating an example of a light emission state of each of the laser emitting element 1 and the LED elements 2A and 2B in a case in which the body 8 has been detected in step S50 in FIG. 12. In the timing chart of FIG. 13, the vertical axis indicates the luminous flux, while the horizontal axis indicates the time. At time $t_0$, the optical measuring apparatus 10 is powered ON. At time $t_1$, physical motion is detected in the optical measuring apparatus 10. At time $t_2$, the body 8 is detected by light emitted from the LED element 2A. At time $t_3$, the body 8 is detected by light emitted from the laser emitting element 1. At time $t_4$, measuring of biological information is finished.

In the standby mode, instead of causing both of the LED elements 2A and 2B to emit light, the CPU 30A causes one of the LED elements 2A and 2B to emit light to detect the body 8. It is thus possible to reduce the amount of light accidentally applied to objects other than the user from the optical measuring apparatus 10 in the standby mode, compared with a case in which both of the LED elements 2A and 2B are caused to emit light with luminous flux $L_{2b}$.

After detecting the body 8 by using light from the LED element 2A, the optical measuring apparatus 10 causes the laser emitting element 1 to emit light. It is thus possible to reduce the amount of light accidentally applied to objects other than the user from the optical measuring apparatus 10 in the standby mode, compared with a case in which both of the laser emitting element 1 and the LED element 2A are caused to emit light after physical motion has been detected in the optical measuring apparatus 10.

In the standby mode after biological information has been measured, all of the laser emitting element 1 and the LED elements 2A and 2B stop emitting light. Hence, after biological information has been measured, when the user removes the optical measuring apparatus 10 from the arm, light is not applied from the optical measuring apparatus 10 to any objects including the user.

Figure 14:
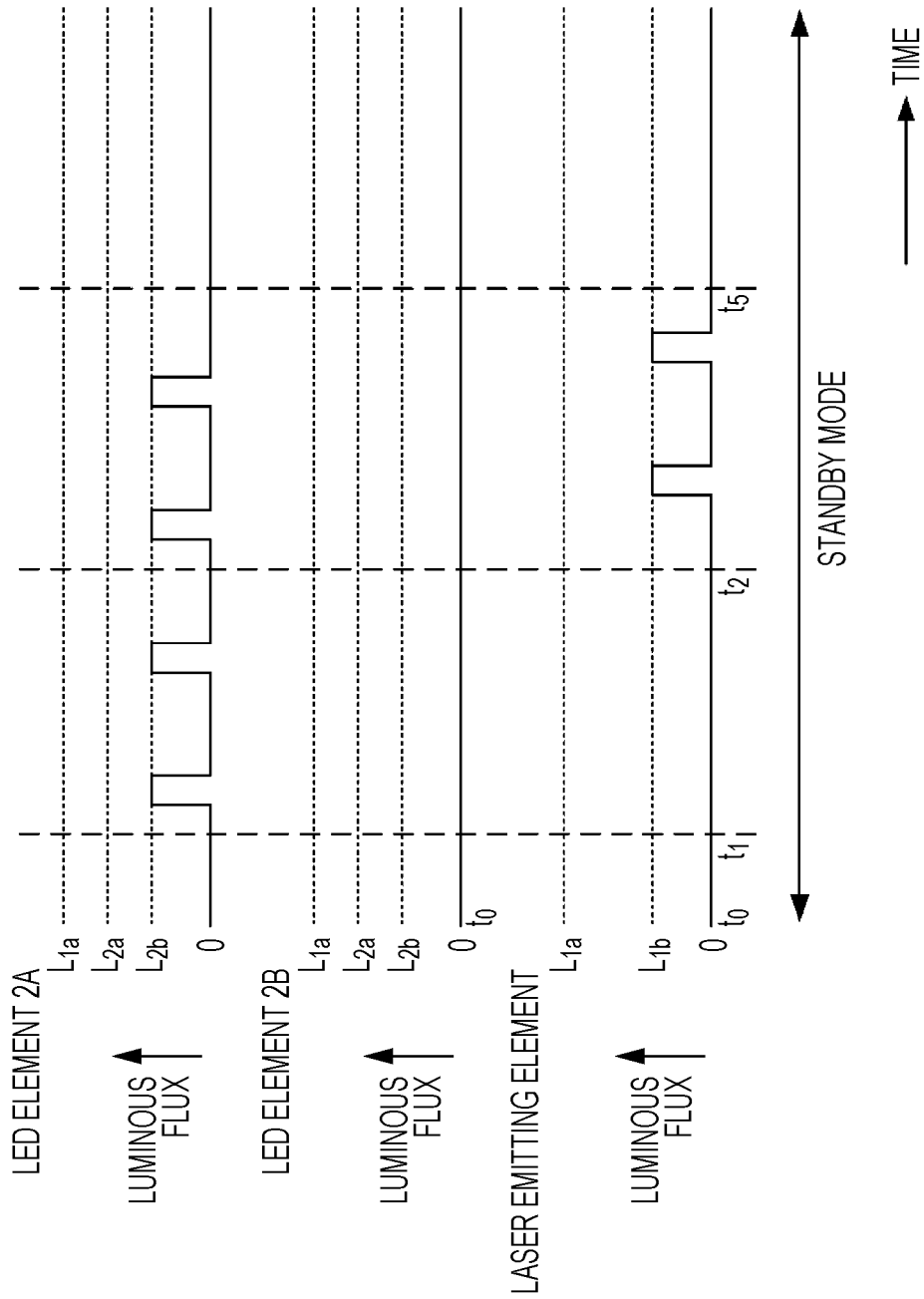
FIG. 14 is a timing chart illustrating an example of a light emission state of each of the laser emitting element and the LED elements according to optical measuring processing shown in FIG. 12.

FIG. 14 is a timing chart illustrating a light emission state of each of the laser emitting element 1 and the LED elements 2A and 2B in a case in which the body 8 has not been detected in step S50 in FIG. 12. At time $t_5$, it is found that the body 8 has not been detected by light emitted from the laser emitting element 1.

In this case, the optical measuring apparatus 10 terminates optical measuring processing without changing the amounts of light emitted from the laser emitting element 1 and the LED elements 2 to those for measuring a body. When the body 8 has not been detected by light from the laser emitting element 1, the laser emitting element 1 and the LED element 2A are caused to stop emitting light, and thus, light is not applied to any objects including the user from the optical measuring apparatus 10.

Various modifications may be made to optical measuring processing shown in FIG. 12. Modified examples of optical measuring processing will be discussed below.

First Modified Example

In optical measuring processing shown in FIG. 12, the LED element 2A is caused to emit light in step S20. However, both of the LED elements 2A and 2B may be caused to emit light with an amount for detecting a body in step S20.

In this case, in step S30, the CPU 30A provisionally calculates percutaneous oxygen saturation according to equations (1) and (2) by using the intensity of light emitted from the LED element 2A and received by the light-receiving element 3 and that from the LED element 2B and received by the light-receiving element 3. If the calculated percutaneous oxygen saturation is contained within a normal range of percutaneous oxygen saturation of a body, the CPU 30A determines that the body 8 has been detected. Then, in step S60, the CPU 30A causes the LED elements 2A and 2B to emit light with an amount for measuring a body to measure percutaneous oxygen saturation. By raising the amount of light emitted from the LED elements 2A and 2B to that for measuring a body, percutaneous oxygen saturation can be measured with a higher precision than in a case in which it is measured with an amount of light for detecting a body.

Second Modified Example

In the above-described exemplary embodiment, the optical measuring apparatus 10 includes both of the laser emitting element 1 and the LED element 2. However, the optical measuring apparatus 10 may include only plural laser emitting elements 1 or only plural LED elements 2.

If the optical measuring apparatus 10 includes only plural laser emitting elements 1, the CPU 30A causes one of the laser emitting elements 1 to emit light with an amount for detecting a body in step S20, instead of causing the LED element 2A to emit light. Then, in step S30, the CPU 30A executes the same processing as step S50 to detect the body 8.

In step S40, the CPU 30A may cause a laser emitting element 1 different from that have emitted light in step S20 to emit light with an amount for detecting a body. The intensity of light received by the light-receiving element 3 may vary depending on the installation locations of the laser emitting elements 1. Using light of different laser emitting elements 1 enhances the precision in detecting the body 8, compared with using light of the same laser emitting element 1 to detect the body 8 multiple times.

In step S60, two laser emitting elements 1 are caused to emit light with an amount for measuring a body, and by using the intensity of light emitted from each of the laser emitting elements 1, percutaneous oxygen saturation is measured. The blood flow rate is measured by using a time change in the intensity of light emitted from one of the laser emitting elements 1 and received by the light-receiving element 3.

If the optical measuring apparatus 10 includes only plural LED elements 2, the CPU 30A causes one of the LED elements 2 to emit light with an amount for detecting a body in step S40, instead of causing the laser emitting element 1 to emit light. Then, in step S50, the CPU 30A executes the same processing as step S30 to detect the body 8.

For the same reason explained when only the laser emitting elements 1 are used, it is preferable that the LED element 2 different from that have emitted light in step S20 be used in step S40.

In step S60, two LED elements 2 are caused to emit light with an amount for measuring a body, and by using the intensity of light emitted from each of the LED elements 2 and received by the light-receiving element 3, percutaneous oxygen saturation is measured. The blood flow rate is measured by using a time change in the intensity of light emitted from one of the LED elements 2 and received by the light-receiving element 3.

Third Modified Example

The optical measuring apparatus 10 includes the LED elements 2A and 2B to measure percutaneous oxygen saturation. However, the optical measuring apparatus 10 may include the LED element 2A only. In this case, pulse waves, which are an example of biological information, are measured by using light from the LED element 2A, and the blood flow rate is measured by using light from the laser emitting element 1.

Biological information measured by the optical measuring apparatus 10 is not limited to pulse waves, blood flow rate, and percutaneous oxygen saturation. The optical measuring apparatus 10 may measure any type of biological information that can be measured optically.

For example, the intensity of light received by the light-receiving element 3 varies according to the pulsation of an artery. The pulse rate can thus be measured by a variation in the intensity of light received by the light-receiving element 3. A variation in the pulse rate is measured in chronological order so as to obtain second derivative waves of photoplethysmogram (SDPTG) (which is also called acceleration plethysmogram (APG)). SDPTG may be used for estimating vascular aging or diagnosing the illness as arteriosclerosis.

Fourth Modified Example

In the above-described exemplary embodiment, the optical measuring apparatus 10 measures biological information by using the same light-emitting elements as those used for detecting the body 8. However, the optical measuring apparatus 10 may use a light-emitting element different from that used for detecting the body 8 to measure biological information.

For example, the optical measuring apparatus 10 may include laser emitting elements 1A and 1B. The laser emitting element 1A is specially used for detecting a body, while the laser emitting element 1B is specially used for measuring biological information. The laser emitting element 1A is caused to emit light with an amount for detecting a body, while the laser emitting element 1B is caused to emit light with an amount for measuring a body. In the optical measuring apparatus 10 of the fourth modified example, the laser emitting element 1A is an example of a first light-emitting element, while the laser emitting element 1B is an example of a second light-emitting element.

The laser emitting element 1A is used as a light source emitting light having wavelengths suitable for detecting a body, while the laser emitting element 1B is used as a light source emitting light having wavelengths suitable for measuring biological information. This may enhance the precision in detecting the body 8 and in measuring biological information, compared with a case in which light-emitting elements emitting light having the same wavelengths are used for detecting the body 8 and for measuring biological information.

Fifth Modified Example

In the above-described exemplary embodiment, the optical measuring apparatus 10 causes the LED element 2 to emit light with an amount for detecting a body to detect the body 8 in step S30 and the laser emitting element 1 to emit light with an amount for detecting a body to detect the body 8 in step S50. However, the optical measuring apparatus 10 may cause the LED element 2 and the laser emitting element 1 to emit light with an amount for measuring a body in steps S30 and S50, respectively. This eliminates the need to raise the amounts of light emitted from the LED element 2A and the laser emitting element 1 to those for measuring a body in step S60. It is thus possible to reduce the time taken to measure biological information, compared with a case in which the body 8 is detected with an amount of light for detecting a body.

Sixth Modified Example

In the above-described exemplary embodiment, the optical measuring apparatus 10 measures a blood flow rate by using light from the laser emitting element 1 and percutaneous oxygen saturation by using light from the LED element 2. However, the laser emitting element 1 and the LED element 2 may not necessarily be used as light sources for measuring different items of biological information.

More specifically, the optical measuring apparatus 10 may use light from the laser emitting element 1 and that from the LED element 2 to measure blood flow rates. Then, the CPU 30A may utilize one of the blood flow rates that has been measured with a higher precision as the measurement result. More specifically, the CPU 30A determines which one of the blood flow rates is closer to a normal blood flow rate that has been set according to the age, gender, and body shape from a medical point of view, and then determines the blood flow rate closer to the normal blood flow rate as that with a higher precision.

The optical measuring apparatus 10 may use plural laser emitting elements 1 and plural LED elements 2 to measure the same item of biological information. More specifically, the optical measuring apparatus 10 may use plural laser emitting elements 1, plural LED elements 2, or a combination of different types of light-emitting elements to measure the same item of biological information. Then, the CPU 30A may utilize one of the plural items of biological information having a higher precision as the measurement result.

Seventh Modified Example

Figure 15:
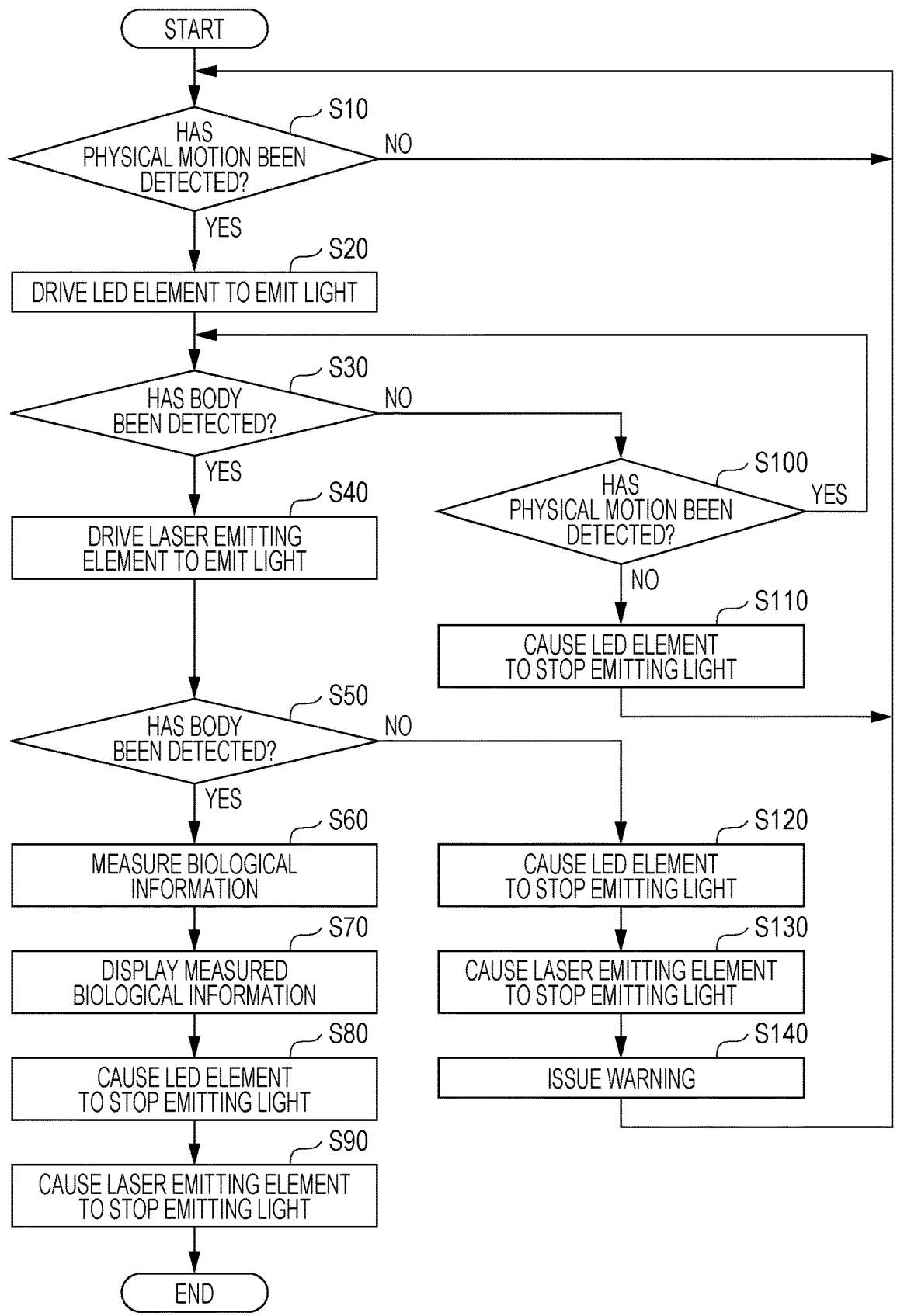
FIG. 15 is a flowchart illustrating an example of a modified example of optical measuring processing shown in FIG. 12.

FIG. 15 illustrates a modified example of optical measuring processing shown in FIG. 12. Optical measuring processing in FIG. 15 is different from that in FIG. 12 in that, after issuing a warning to inform the user of a failure to detect the body 8 in step S140, the CPU 30A returns to step S10, instead of terminating optical measuring processing.

The optical measuring apparatus 10 causes the LED element 2A to stop emitting light in step S120 and the laser emitting element 1 to stop emitting light in step S130. Accordingly, after the detection of physical motion in the optical measuring apparatus 10 is restarted, light is not emitted from the optical measuring apparatus 10 until physical motion is applied to the optical measuring apparatus 10.

Eighth Modified Example

Figure 16:
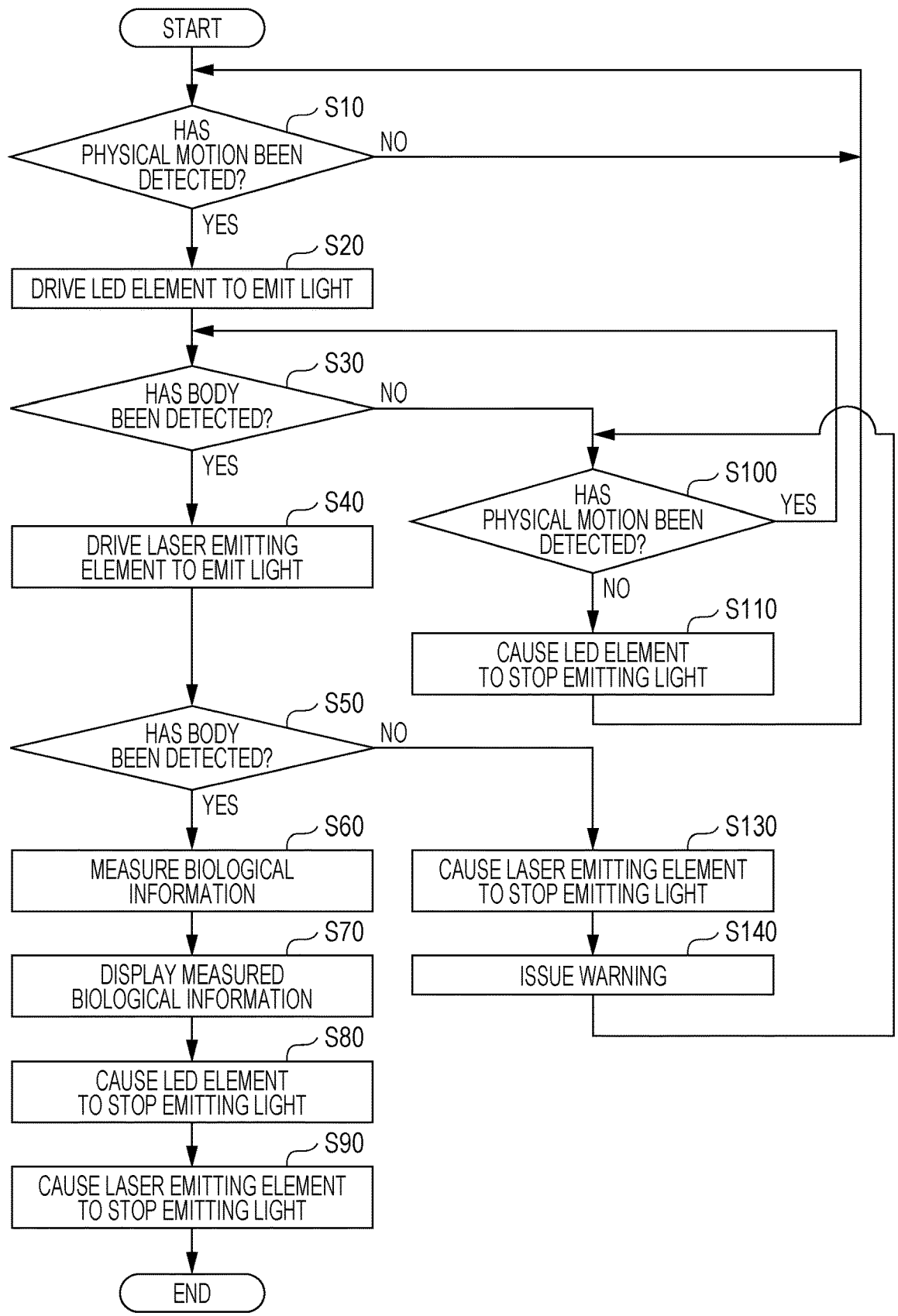
FIG. 16 is a flowchart illustrating an example of a modified example of optical measuring processing shown in FIG. 12.

FIG. 16 illustrates a modified example of optical measuring processing shown in FIG. 12. Optical measuring processing in FIG. 16 is different from that in FIG. 12 in that step S120 is deleted, and after step S140, the CPU 30A returns to step S100 to redetect the body 8.

As a result of deleting step S120, the CPU 30A returns to step S100 to redetect the body 8 while maintaining the amount of light emitted from the LED element 2A at that for detecting a body. It is thus possible to reduce the time taken to measure biological information, compared with a case in which light emission of the LED element 2A is stopped and the amount of light from the LED element 2A is raised again to that for detecting a body.

In optical measuring processing in FIG. 16, if the result of step S50 is NO, the CPU 130A proceeds to step S130 while maintaining the amount of light emitted from the LED element 2A at that for detecting a body. Alternatively, the amount of light from the LED element 2A may be reduced to that lower than the amount for detecting a body. In this case, after physical motion is detected in step S100, the CPU 130A raises the amount of light from the LED element 2A to that for detecting a body and detects the body 8 in step S30. This makes it possible to reduce the amount of light emitted from the optical measuring apparatus 10 while physical motion in the optical measuring apparatus 10 is being detected, compared with a case in which motion in the optical measuring apparatus 10 is detected with the amount of light for detecting a body.

In optical measuring processing in FIG. 16, the laser emitting element 1 is caused to stop emitting light in step S130. Alternatively, the amount of light from the laser emitting element 1 may be reduced to that for detecting a body. It is thus possible to reduce the time taken to measure biological information, compared with a case in which light emission of the laser emitting element 1 is stopped and the amount of light from the laser emitting element 1 is raised again to that for detecting a body in step S40.

Figure 17:
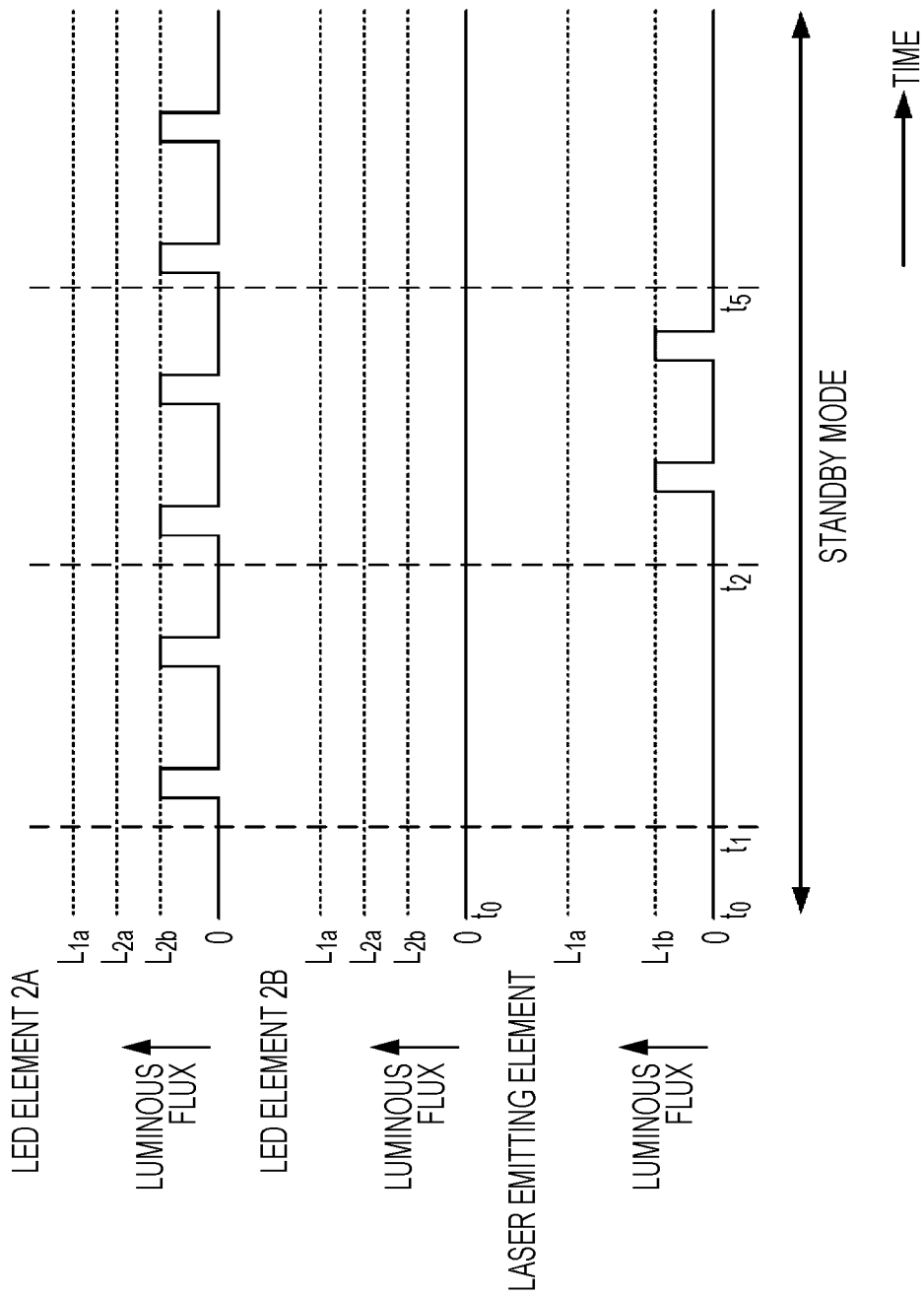
FIG. 17 is a timing chart illustrating an example of a light emission state of each of the laser emitting element and the LED elements according to a modified example of optical measuring processing shown in FIG. 12.

FIG. 17 is a timing chart illustrating an example of a light emission state of each of the laser emitting element 1 and the LED elements 2A and 2B in a case in which the body 8 has not been detected in step S50 in FIG. 16.

FIG. 17 shows that, even after the body 8 has not been detected by light emitted from the laser emitting element 1, the optical measuring apparatus 10 keeps the LED element 2A emitting light with an amount for detecting a body to redetect the body 8.

Ninth Modified Example

In optical measuring processing in FIG. 12, the body 8 is detected by light emitted from the laser emitting element 1 and that from the LED element 2. However, the body 8 may be detected without causing the laser emitting element 1 and the LED element 2 to emit light.

Figure 18:
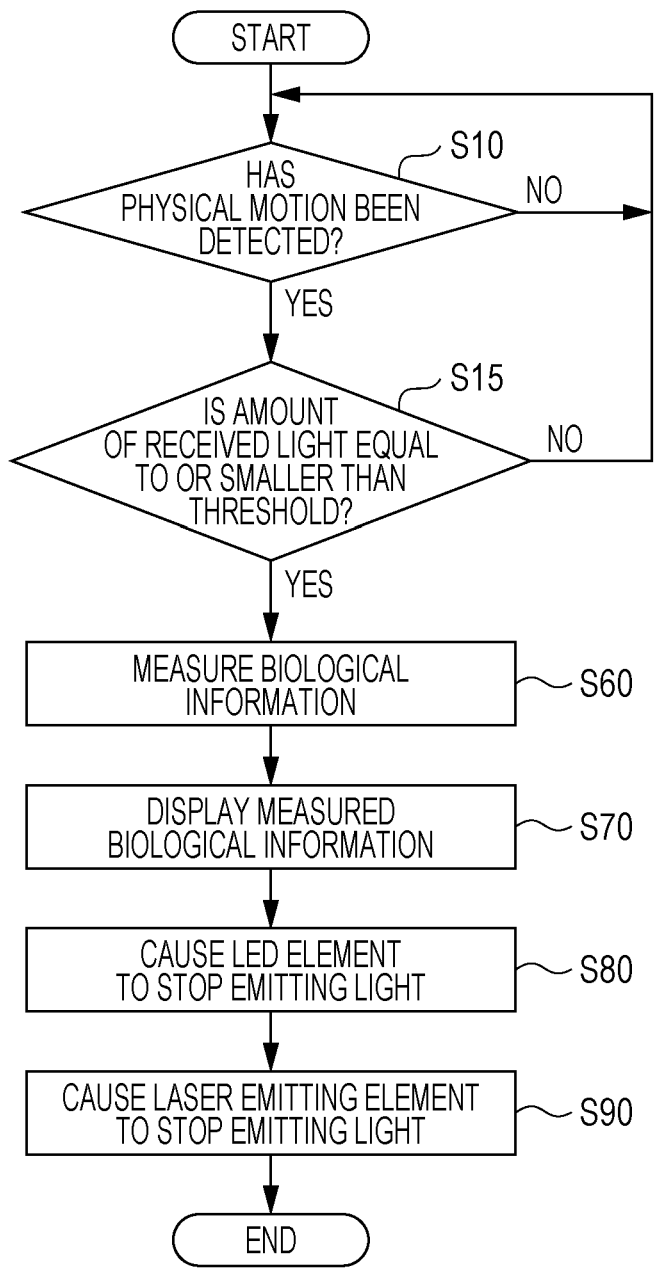
FIG. 18 is a flowchart illustrating an example of a modified example of optical measuring processing shown in FIG. 12.

FIG. 18 is a flowchart illustrating an example of optical measuring processing for detecting the body 8 without causing the laser emitting element 1 and the LED element 2 to emit light.

Optical measuring processing in FIG. 18 is different from that in FIG. 12 in that steps S20 through S50 and S100 through S140 are deleted and step S15 is added.

In step S15, in a state in which light emission of all of the laser emitting element 1 and the LED elements 2 has stopped, the CPU 30A calculates the amount of light received by the light-receiving element 3 per unit time, for example, by using the intensity of received light and digitized by the A/D converter circuit 18.

When the user wears the optical measuring apparatus 10 on the arm in the daytime or in a room with lighting ON, the amount of light received by the light-receiving element 3 becomes less than that before the user wears the optical measuring apparatus 10 because the light-receiving element 3 is covered by the arm.

A threshold for the amount of light received by the light-receiving element 3 is set in advance. If the amount of received light is equal to or smaller than this threshold, it is assumed that the optical measuring apparatus 10 is attached to the body 8. This threshold may be called a body detection threshold. The CPU 30A determines in step S15 whether the calculated amount of received light is equal to or smaller than the body detection threshold. The body detection threshold may be found by experiment using an actual product of the optical measuring apparatus 10 or by computer simulations based on the design specifications of the optical measuring apparatus 10, and may be stored in the non-volatile memory 30D.

If the calculated amount of received light exceeds the body detection threshold, it is unlikely that the optical measuring apparatus 10 is attached to the body 8. The CPU 30A thus returns to step S10 to monitor the output value of the motion sensor 38 until the user touches the optical measuring apparatus 10.

If the calculated amount of received light is equal to or smaller than the body detection threshold, it is likely that the optical measuring apparatus 10 is attached to the body 8. Then, the CPU 30A proceeds to step S60. In step S60, the CPU 30A causes the laser emitting element 1 and the LED element 2 to emit light with the corresponding amounts for measuring a body to measure a blood flow rate and percutaneous oxygen saturation of the user.

If the body 8 is detected based on a change in the amount of light received by the light-receiving element 3, light is not emitted from the optical measuring apparatus 10 in the standby mode. It is thus possible to reduce the amount of light accidentally emitted to objects other than the user from the optical measuring apparatus 10.

The exemplary embodiment has been discussed above. However, the present invention is not restricted to the range of the above-described exemplary embodiment. Various modifications and improvements may be made without departing from the spirit and scope of the invention. Exemplary embodiments implemented by making various modifications and improvements are also encompassed within the technical scope of the invention.

For example, optical measuring processing shown in FIGS. 12, 15, 16, and 18 may be implemented by using hardware, such as an application specific integrated circuit (ASIC). In this case, optical measuring processing may be executed faster than that implemented by software.

As discussed in the exemplary embodiment, the presence or the absence of a body is determined according to whether the value representing biological information, such as pulse waves or percutaneous oxygen saturation, measured by light emitted from a first light-emitting element is within a predetermined range which indicates the presence of a body. However, this is only an example. The presence or the absence of a body may be determined based on another factor. For example, configuration information indicating the configuration of a subject to be measured may be detected by light emitted from the first light-emitting element, and the presence or the absence of a body may be determined based on this configuration information. If features representing the configuration of a face, for example, are detected as the configuration information, the presence of a body may be determined.

A subject to be measured by the optical measuring apparatus 10 is not restricted to a body. The optical measuring apparatus 10 may be used for other purposes. For example, the optical measuring apparatus 10 may be a device that judges whether a steel sheet has a flaw by applying light thereto and then determines the position and degree of a flaw, based on the intensity of light received by the light-receiving element 3. The optical measuring apparatus 10 may be a device that measures the spectral transmittance and reflectance of an optical element, such as a lens. The optical measuring apparatus 10 may be a device that determines components of a subject, such as a fruit, by emitting light to the fruit and receiving light reflected by the fruit, and measures a sugar content, for example, contained in the fruit.

Although the optical measuring program is installed in the ROM 30B in the exemplary embodiment, it may be provided as a result of being recorded in a computer-readable storage medium. For example, the optical measuring program may be provided as a result of being recorded in an optical disc, such as a compact disc (CD)-ROM or a digital versatile disc (DVD)-ROM, or in a semiconductor memory, such as a universal serial bus (USB) memory or a memory card. The optical measuring program may be obtained from an external device via a communication network connected to the communication device 37.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An optical measuring apparatus comprising:
   first and second light-emitting elements that emit light, the first light-emitting element including a first LED element and a second LED element that emit different wavelengths of light; and
   a controller that performs a first control so that,
      the first LED element initially emits light at a first intensity,
      only in response to a first detection of a presence of a body by the light emitted from the first LED element of the first light-emitting element at the first intensity, the second light-emitting element emits light at a second intensity during a period in which the first LED element continues to emit light at the first intensity,
      in response to a second detection of the presence of the body by the light emitted from the second light-emitting element at the second intensity, the second detection of the presence of the body being based on (a) a spectral distribution detected using the light emitted by the second light-emitting element at the second intensity and (b) an intensity of a predetermined frequency of the detected spectral distribution,
         (i) the first LED element and the second LED element emit light with an amount for measuring first biological information of the body, the light emitted from the first LED element for measuring the first biological information of the body being emitted at a third intensity greater than the first intensity, and
         (ii) the second light-emitting element emits light with an amount for measuring second biological information of the body at a timing that does not overlap with a timing at which the first light-emitting element emits light for measuring the first biological information of the body, the light emitted from the second light-emitting element for measuring the second biological information of the body being emitted at a fourth intensity greater than the second and third intensities.

2. The optical measuring apparatus according to claim 1, wherein an amount of the light emitted from the first light-emitting element is less than the amount of the light emitted from the second light-emitting element for measuring the second biological information of the body.

3. The optical measuring apparatus according to claim 1, further comprising:
   a measuring unit that measures the first biological information concerning the body by using the light emitted from the first light-emitting element and measures the second biological information concerning the body by using the light emitted from the second light-emitting element, the second biological information being different from the first biological information.

4. The optical measuring apparatus according to claim 3, wherein the measuring unit measures at least one of pulse waves and percutaneous oxygen saturation of the body by using the light emitted from the first light-emitting element, and measures a blood flow rate of the body by using the light emitted from the second light-emitting element.

5. The optical measuring apparatus according to claim 1, wherein the second light-emitting element is a laser element.

6. The optical measuring apparatus according to claim 5, further comprising:
   a measuring unit that measures the first biological information concerning the body by using the light emitted from the first light-emitting element and measures the second biological information concerning the body by using the light emitted from the second light-emitting element, the second biological information being different from the first biological information.

7. The optical measuring apparatus according to claim 6, wherein the measuring unit measures at least one of pulse waves and percutaneous oxygen saturation of the body by using the light emitted from the first light-emitting element, and measures a blood flow rate of the body by using the light emitted from the second light-emitting element.

8. The optical measuring apparatus according to claim 1, wherein, upon detection of pulse waves of the body by the light emitted from the first light-emitting element, the controller causes the second light-emitting element to emit light with the amount for measuring the body.

9. The optical measuring apparatus according to claim 1, wherein the controller performs the first control so that an amount of the light emitted from the second light-emitting element will be regulated to be less than the amount for measuring the second biological information of the body until the presence of the body is detected by the light emitted from the first light-emitting element.

10. The optical measuring apparatus according to claim 1, wherein,
the light emitted by the second light-emitting element is also for detecting the presence of the body, and
the controller performs a second control so that, when the presence of the body is detected by the light emitted from the first light-emitting element and the presence of the body is not detected by the light emitted from the second light-emitting element, an amount of the light emitted from the second light-emitting element will be regulated to be less than the amount for measuring the second biological information of the body.

11. The optical measuring apparatus according to claim 10, wherein, the second control further includes control so that an amount of the light emitted from the first light-emitting element will be reduced to be less than an amount of the light emitted from the first light-emitting element used for detecting the presence of the body.

12. The optical measuring apparatus according to claim 1, further comprising:
a measuring unit that measures the first biological information concerning the body by using the light emitted from the first light-emitting element and measures the second biological information concerning the body by using the light emitted from the second light-emitting element, the second biological information being different from the first biological information, wherein,
the light emitted by the second light-emitting element is also for detecting the presence of the body, and
the controller performs a third control so that, upon detection of the presence of the body by the light emitted from the first light-emitting element and also by the light emitted from the second light-emitting element, each of the first and second light-emitting elements will emit light with the amount for measuring the body.

13. The optical measuring apparatus according to claim 1, further comprising:
a motion sensor that detects motion of the optical measuring apparatus, wherein
the controller turns the first light-emitting element on in response to the motion sensor detecting the motion of the optical measuring apparatus.

14. The optical measuring apparatus according to claim 1, wherein
the controller performs the control upon the detection of the presence of the body by visible light emitted from the first light-emitting element, so that the second light-emitting element will emit invisible light with the amount for measuring the second biological information of the body.

15. An optical measuring apparatus comprising:
a light emitting element including a first light-emitting diode and a second light-emitting diode that emit different wavelengths of light;
a laser element; and
a controller that performs control so that,
the first light-emitting diode initially emits light at a first intensity,
only in response to a first detection of a presence of a body by the light emitted from the first light-emitting diode at the first intensity, the laser element emits light at a second intensity during a period in which the first light-emitting diode continues to emit light at the first intensity,
in response to a second detection of the presence of the body by the light emitted from the laser element at the second intensity, the second detection of the presence of the body being based on (a) a spectral distribution detected using the light emitted by the laser element at the second intensity and (b) an intensity of a predetermined frequency of the detected spectral distribution,
(i) the first light-emitting diode and the second light-emitting diode emit light with an amount for measuring first biological information of the body, the light emitted from the first light-emitting diode for measuring the first biological information of the body being emitted at a third intensity greater than the first intensity, and
(ii) the laser element emits light with an amount for measuring second biological information of the body at a timing that does not overlap with a timing at which the light-emitting element emits light for measuring the first biological information of the body, the light emitted from the laser element for measuring the second biological information of the body being emitted at a fourth intensity greater than the second and third intensities.

16. The optical measuring apparatus according to claim 15, further comprising:
a motion sensor that detects motion of the optical measuring apparatus, wherein
the controller turns the first light-emitting diode on in response to the motion sensor detecting the motion of the optical measuring apparatus.

17. The optical measuring apparatus according to claim 13, wherein
the controller performs the control upon the detection of the presence of the body by visible light emitted from the light-emitting element, so that the laser element will emit invisible light with the amount for measuring the second biological information of the body.

18. A non-transitory computer readable medium storing a program causing a computer to execute a process, the process comprising:
causing a first light-emitting element to emit light, the first light-emitting element including a first LED element and a second LED element that emit different wavelengths of light; and
performing a first control so that,
the first LED element initially emits light at a first intensity,
only in response to a first detection of a presence of a body by the light emitted from the first LED element of the first light-emitting element at the first intensity, the second light-emitting element emits light at a second intensity during a period in which the first LED element continues to emit light at the first intensity, in response to a second detection of the presence of the body by the light emitted from the second light-emitting element at the second intensity, the second detection of the presence of the body being based on (a) a spectral distribution detected using the light emitted by the second light-emitting element at the second intensity and (b) an intensity of a predetermined frequency of the detected spectral distribution,
- (i) the first LED element and the second LED element emit light with an amount for measuring first biological information of the body, the light emitted from the first LED element for measuring the first biological information of the body being emitted at a third intensity greater than the first intensity of the light, and
- (ii) a second light-emitting element emits light with an amount for measuring second biological information of the body at a timing that does not overlap with a timing at which the first light-emitting element emits light for measuring the first biological information of the body, the light emitted from the second light-emitting element for measuring the second biological information of the body being emitted at a fourth intensity greater than the second and third intensities.

19. The non-transitory computer readable medium according to claim 18, the process further comprising:
    detecting a motion using a motion sensor included in an optical measuring apparatus having the first and second light-emitting elements; and
    turning the first light-emitting element on in response to the motion sensor detecting the motion of the optical measuring apparatus.

20. The non-transitory computer readable medium according to claim 14, wherein
    the first control is performed upon the detection of the presence of the body by visible light emitted from the first light-emitting element, so that the second light-emitting element will emit invisible light with the amount for measuring the second biological information of the body.

* * * * *